United States Patent
Burnett et al.

(10) Patent No.: US 9,498,366 B2
(45) Date of Patent: Nov. 22, 2016

(54) DEVICES AND METHODS FOR PYLORIC ANCHORING

(75) Inventors: Daniel R. Burnett, San Francisco, CA (US); Gregory W. Hall, Redwood City, CA (US); Annette Campbell-White, Oakland, CA (US); Jordan T. Bajor, Palo Alto, CA (US)

(73) Assignee: BAROnova, Inc., San Carlos, CA (US)

( * ) Notice: Subject to any disclaimer, the term of this patent is extended or adjusted under 35 U.S.C. 154(b) by 1334 days.

(21) Appl. No.: 10/915,716

(22) Filed: Aug. 9, 2004

(65) Prior Publication Data
US 2005/0055039 A1 Mar. 10, 2005

Related U.S. Application Data

(63) Continuation-in-part of application No. 10/833,950, filed on Apr. 27, 2004, now Pat. No. 8,048,169, which (Continued)

(51) Int. Cl.
*A61B 17/08* (2006.01)
*A61F 5/00* (2006.01)
(Continued)

(52) U.S. Cl.
CPC ......... *A61F 5/0079* (2013.01); *A61B 5/14539* (2013.01); *A61B 5/14546* (2013.01);
(Continued)

(58) Field of Classification Search
CPC .... A61F 2/0063; A61F 5/0036; A61F 5/003; A61F 5/0079; A61B 17/122; A61B 17/00234; A61B 5/4238; A61B 5/14539; A61B 17/12036; A61B 17/12136; A61B 17/1219; A61B 5/14546; A61B 17/12022; A61B 17/12099; A61B 17/12172
USPC ....... 623/23.64, 23.65, 23.71; 606/151, 157; 600/37
See application file for complete search history.

(56) References Cited

U.S. PATENT DOCUMENTS 2,499,045 A 2/1950 Ray et al.
3,154,077 A 10/1964 Cannon
(Continued)

FOREIGN PATENT DOCUMENTS

DE 4012642 10/1991
WO WO 88/00027 1/1988
(Continued)

OTHER PUBLICATIONS

U.S. Appl. No. 10/671,191, filed Sep. 24, 2003 in the name of Burnett, Final Office Action mailed May 5, 2005.
(Continued)

*Primary Examiner* — Gregory Anderson
*Assistant Examiner* — Son Dang
(74) *Attorney, Agent, or Firm* — Levine Bagade Han LLP

(57) ABSTRACT

A device for performing one or more functions in a gastrointestinal tract of a patient includes an anchoring member and at least one actuator, sensor, or combination of both coupled with the anchoring device. The anchoring device is adapted to maintain at least part of the device within a pyloric portion of the patient's stomach and to intermittently engage, without directly attaching to, stomach tissue. Actuators perform any suitable function, such as transmitting energy to tissue, acting as a sleeve to reduce nutrient absorption, occupying space in the stomach, eluting a drug and/or the like. Sensors may be adapted to sense any suitable patient characteristic within the patient's gastrointestinal tract, such as pH, temperature, bile content, nutrient content, fats, sugars, alcohol, opiates, drugs, analytes, electrolytes and/or hemoglobin.

26 Claims, 27 Drawing Sheets

Related U.S. Application Data is a continuation-in-part of application No. 10/671,191, filed on Sep. 24, 2003, now Pat. No. 6,994,095.

(60) Provisional application No. 60/525,105, filed on Nov. 26, 2003, provisional application No. 60/490,421, filed on Jul. 28, 2003.

(51) Int. Cl.
| | |
|---|---|
| *A61B 5/00* | (2006.01) |
| *A61B 17/12* | (2006.01) |
| *A61B 5/03* | (2006.01) |
| *A61B 5/07* | (2006.01) |
| *A61B 5/145* | (2006.01) |
| *A61B 17/00* | (2006.01) |
| *A61F 2/24* | (2006.01) |
| *A61F 2/04* | (2013.01) |
| *A61N 1/06* | (2006.01) |
| *A61N 1/40* | (2006.01) |

(52) U.S. Cl.
CPC .......... *A61B 5/4238* (2013.01); *A61B 17/1219* (2013.01); *A61B 17/12022* (2013.01); *A61B 17/12036* (2013.01); *A61B 17/12099* (2013.01); *A61B 17/12136* (2013.01); *A61B 17/12172* (2013.01); *A61F 5/003* (2013.01); *A61F 5/0036* (2013.01); *A61B 5/036* (2013.01); *A61B 5/073* (2013.01); *A61B 5/145* (2013.01); *A61B 2017/00876* (2013.01); *A61B 2017/12054* (2013.01); *A61B 2017/12086* (2013.01); *A61F 2/24* (2013.01); *A61F 2002/044* (2013.01); *A61N 1/06* (2013.01); *A61N 1/40* (2013.01)

(56) References Cited

U.S. PATENT DOCUMENTS

| | | |
|---|---|---|
| 3,915,171 A | 10/1975 | Shermeta |
| 4,133,315 A | 1/1979 | Berman et al. |
| 4,240,412 A | 12/1980 | James |
| 4,246,893 A | 1/1981 | Berson |
| 4,315,509 A | 2/1982 | Smit |
| 4,368,739 A | 1/1983 | Nelson |
| 4,416,267 A | 11/1983 | Garren et al. |
| 4,485,805 A | 12/1984 | Foster, Jr. |
| 4,517,979 A | 5/1985 | Pecenka |
| 4,598,699 A | 7/1986 | Garren et al. |
| 4,648,383 A | 3/1987 | Angelchik |
| 4,657,020 A | 4/1987 | Lifton |
| 4,694,827 A | 9/1987 | Weiner et al. |
| 4,735,214 A | 4/1988 | Berman |
| 4,762,128 A | 8/1988 | Rosenbluth |
| 4,836,204 A | 6/1989 | Landymore et al. |
| 4,878,905 A | 11/1989 | Blass |
| 4,925,446 A | 5/1990 | Garay et al. |
| 4,930,496 A | 6/1990 | Bosley |
| 4,946,440 A | 8/1990 | Hall |
| 5,011,488 A | 4/1991 | Ginsburg |
| 5,108,420 A | 4/1992 | Marks |
| 5,129,915 A | 7/1992 | Cantenys |
| 5,192,301 A | 3/1993 | Kamiya et al. |
| 5,246,445 A | 9/1993 | Yachia et al. |
| 5,282,829 A | 2/1994 | Hermes |
| 5,306,300 A | 4/1994 | Berry |
| 5,312,343 A | 5/1994 | Krog et al. |
| 5,423,872 A | 6/1995 | Cigaina |
| 5,509,888 A | 4/1996 | Miller |
| 5,514,091 A | 5/1996 | Yoon |
| 5,514,178 A | 5/1996 | Torchio |
| 5,540,701 A | 7/1996 | Sharkey et al. |
| 5,545,210 A | 8/1996 | Hess et al. |
| 5,634,936 A | 6/1997 | Linden et al. |
| 5,674,192 A | 10/1997 | Sahatjian et al. |
| 5,676,688 A | 10/1997 | Jaker et al. |
| 5,707,355 A | 1/1998 | Zimmon |
| 5,750,585 A | 5/1998 | Park et al. |
| 5,752,971 A | 5/1998 | Rosenbluth et al. |
| 5,782,800 A | 7/1998 | Yoon |
| 5,820,584 A | 10/1998 | Crabb |
| 5,853,422 A | 12/1998 | Huebsch et al. |
| 5,947,991 A | 9/1999 | Cowan |
| 5,976,174 A | 11/1999 | Ruiz |
| 6,067,991 A | 5/2000 | Forsell |
| 6,102,928 A | 8/2000 | Bonutti |
| 6,112,703 A | 9/2000 | Handelsman |
| 6,117,159 A | 9/2000 | Huebsch et al. |
| 6,152,144 A | 11/2000 | Lesh et al. |
| 6,159,219 A | 12/2000 | Ren |
| 6,162,201 A | 12/2000 | Cohen |
| 6,183,520 B1 | 2/2001 | Pintauro et al. |
| 6,245,090 B1 | 6/2001 | Gilson et al. |
| 6,270,515 B1 | 8/2001 | Linden et al. |
| 6,371,974 B1 | 4/2002 | Brenneman et al. |
| 6,409,656 B1 | 6/2002 | Sangouard et al. |
| 6,488,962 B1 | 12/2002 | Berner et al. |
| 6,527,701 B1 | 3/2003 | Sayet et al. |
| 6,527,739 B1 | 3/2003 | Bigus et al. |
| 6,540,789 B1 | 4/2003 | Silverman et al. |
| 6,544,291 B2 | 4/2003 | Taylor |
| 6,558,400 B2 | 5/2003 | Deem et al. |
| 6,579,301 B1 | 6/2003 | Bales et al. |
| 6,600,953 B2 | 7/2003 | Flesler et al. |
| 6,652,578 B2 | 11/2003 | Bailey et al. |
| 6,675,809 B2 * | 1/2004 | Stack et al. .................. 128/898 |
| 6,689,046 B2 | 2/2004 | Sayet et al. |
| 6,702,846 B2 | 3/2004 | Mikus |
| 6,740,121 B2 | 5/2004 | Geitz |
| 6,755,869 B2 | 6/2004 | Geitz |
| 6,802,868 B2 | 10/2004 | Silverman et al. |
| 6,860,895 B1 | 3/2005 | Akerfeldt et al. |
| 6,994,095 B2 | 2/2006 | Burnett |
| 7,011,621 B2 | 3/2006 | Sayet et al. |
| 7,037,344 B2 | 5/2006 | Kagan et al. |
| 7,054,690 B2 | 5/2006 | Imran et al. |
| 7,087,072 B2 | 8/2006 | Marino et al. |
| 7,120,498 B2 | 10/2006 | Imran et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,160,312 B2 | 1/2007 | Saadat |
| 7,167,750 B2 | 1/2007 | Knudson et al. |
| 7,186,251 B2 | 3/2007 | Malecki et al. |
| 7,320,696 B2 | 1/2008 | Gazi et al. |
| 7,588,584 B2 | 9/2009 | Fogarty et al. |
| 7,842,053 B2 | 11/2010 | Chanduszko et al. |
| 8,048,169 B2 | 11/2011 | Burnett et al. |
| 8,257,389 B2 | 9/2012 | Chanduszko et al. |
| 2002/0013601 A1 | 1/2002 | Nobles et al. |
| 2002/0038100 A1 | 3/2002 | Okada |
| 2002/0091395 A1 | 7/2002 | Gabbay |
| 2002/0165589 A1 * | 11/2002 | Imran et al. .................... 607/40 |
| 2002/0188354 A1 | 12/2002 | Peghini |
| 2002/0198470 A1 | 12/2002 | Imran et al. |
| 2002/0198570 A1 | 12/2002 | Puskas |
| 2003/0023150 A1 | 1/2003 | Yokoi et al. |
| 2003/0040804 A1 | 2/2003 | Stack et al. |
| 2003/0078611 A1 | 4/2003 | Hashiba et al. |
| 2003/0093117 A1 | 5/2003 | Saadat |
| 2003/0109931 A1 | 6/2003 | Geitz |
| 2003/0109935 A1 | 6/2003 | Geitz |
| 2003/0120328 A1 | 6/2003 | Jenkins et al. |
| 2003/0144708 A1 | 7/2003 | Starkebaum |
| 2003/0153806 A1 | 8/2003 | Miller |
| 2003/0158601 A1 | 8/2003 | Silverman et al. |
| 2004/0034408 A1 | 2/2004 | Majercack |
| 2004/0059368 A1 | 3/2004 | Maryanka |
| 2004/0107004 A1 | 6/2004 | Levine et al. |
| 2004/0117031 A1 | 6/2004 | Stack et al. |
| 2004/0158331 A1 | 8/2004 | Stack et al. |
| 2004/0172141 A1 | 9/2004 | Stack et al. |

(56) References Cited

U.S. PATENT DOCUMENTS

| | | |
|---|---|---|
| 2004/0172142 A1 | 9/2004 | Stack et al. |
| 2004/0213825 A1 | 10/2004 | Levy |
| 2004/0230222 A1 | 11/2004 | van der Burg et al. |
| 2004/0236357 A1 | 11/2004 | Kraemer et al. |
| 2004/0267378 A1 | 12/2004 | Gazi et al. |
| 2005/0033331 A1 | 2/2005 | Burnett et al. |
| 2005/0033332 A1 | 2/2005 | Burnett |
| 2005/0038460 A1 | 2/2005 | Jayaraman |
| 2005/0038470 A1 | 2/2005 | Van Der Burg et al. |
| 2005/0055039 A1 | 3/2005 | Burnett et al. |
| 2005/0064009 A1 | 3/2005 | Bates |
| 2005/0090873 A1 | 4/2005 | Imran et al. |
| 2005/0096673 A1 | 5/2005 | Stack et al. |
| 2005/0149142 A1 | 7/2005 | Starkebaum |
| 2005/0192627 A1 | 9/2005 | Whisenant et al. |
| 2005/0192629 A1 | 9/2005 | Saadat et al. |
| 2005/0273060 A1 | 12/2005 | Levy et al. |
| 2005/0288786 A1 | 12/2005 | Chanduszko |
| 2006/0020278 A1 | 1/2006 | Burnett et al. |
| 2006/0178691 A1 | 8/2006 | Binmoeller |
| 2006/0217763 A1 | 9/2006 | Abbott et al. |
| 2006/0259074 A1 | 11/2006 | Kelleher et al. |
| 2006/0282107 A1 | 12/2006 | Hashiba et al. |
| 2006/0293742 A1 | 12/2006 | Dann et al. |
| 2007/0016262 A1 | 1/2007 | Gross et al. |
| 2007/0027548 A1 | 2/2007 | Levine et al. |
| 2007/0056591 A1 | 3/2007 | McSwain |
| 2007/0083224 A1 | 4/2007 | Hively |
| 2007/0135831 A1 | 6/2007 | Burnett et al. |
| 2007/0178160 A1 | 8/2007 | Burnett |
| 2007/0198082 A1 | 8/2007 | Kapadia et al. |
| 2007/0239284 A1 | 10/2007 | Skerven et al. |
| 2007/0250132 A1 | 10/2007 | Burnett |
| 2009/0118757 A1 | 5/2009 | Burnett et al. |
| 2009/0118758 A1 | 5/2009 | Burnett et al. |
| 2009/0177288 A1 | 7/2009 | Wallsten |
| 2009/0182357 A1 | 7/2009 | Burnett et al. |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0198210 A1 | 8/2009 | Burnett et al. |
| 2009/0216262 A1 | 8/2009 | Burnett et al. |
| 2009/0299486 A1 | 12/2009 | Shohat et al. |

FOREIGN PATENT DOCUMENTS

| | | |
|---|---|---|
| WO | WO 90/00369 | 1/1990 |
| WO | WO 02/091961 A1 | 11/2002 |
| WO | WO 03/017882 A2 | 3/2003 |
| WO | WO 2005/009288 | 2/2005 |
| WO | WO 2006/135857 | 12/2006 |
| WO | WO 2007/027812 | 3/2007 |

OTHER PUBLICATIONS

U.S. Appl. No. 10/671,191, filed Sep. 24, 2003 in the name of Burnett, Non-final Office Action mailed Dec. 15, 2004.
U.S. Appl. No. 10/671,191, filed Sep. 24, 2003 in the name of Burnett, Notice of Allowance mailed Sep. 13, 2005.
U.S. Appl. No. 10/833,950, filed Apr. 27, 2004 in the name of Burnett et al., Non-final Office Action mailed Apr. 15, 2009.
U.S. Appl. No. 11/215,430, filed Aug. 29, 2005 in the name of Burnett et al., Final Office Action mailed May 28, 2008.
U.S. Appl. No. 11/215 430, filed Aug. 29, 2005 in the name of Burnett et al., Non-final Office Action mailed Feb. 13, 2009.
U.S. Appl. No. 11/215,430, filed Aug. 29 2005 in the name of Burnett et al., Non-final Office Action mailed Mar. 8, 2007.
International Patent Application No. PCT/US2005/026370 filed Jul. 25, 2005 in the name of Baronova, Inc., International Search Report and Written Opinion mailed Sep. 30, 2008.
International Patent Application No. PCT/US2007/003052 filed Feb. 5, 2007 in the name of Baronova, Inc., International Search Report and Written Opinion mailed Nov. 19, 2007.
International Patent Application No. PCT/US2007/003260 filed Feb. 5, 2007 in the name of Baronova, Inc., International Search Report and Written Opinion mailed Sep. 26, 2008.
International Patent Application No. PCT/US2008/075439 filed Sep. 5, 2008 in the name of Baronova, Inc., International Search Report and Written Opinion mailed Nov. 10, 2008.
International Patent Application No. PCT/US2006/033923 filed Aug. 29, 2006 in the name of Baronova, Inc., International Search Report and Written Opinion mailed Jan. 18, 2008.
International Patent Application No. PCT/US2004/023470 filed Jul. 20, 2004 in the name of Polymorfix, Inc., International Search Report and Written Opinion mailed May 27, 2005.
European Patent Application No. 04778818.7 filed Jul. 20, 2004 in the name of Burnett et al., Office Action mailed Oct. 5, 2009.
European Patent Application No. 05774631.5 filed Jul. 25, 2005 in the name of Burnett et al., Supplementary Partial European Search Report and Opinion mailed Dec. 1, 2009.
European Patent Application No. 05774631.5 filed Jul. 25, 2005 in the name of Burnett et al., Office Action mailed Mar. 16, 2010.
Canadian Patent Application No. 2,534,118 filed Jul. 20, 2004 in the name of Burnett et al., Office Action mailed Apr. 1, 2010.
European Patent Application No. 07763667.8 filed Feb. 5, 2007 in the name of Burnett, Search Report and Opinion mailed Dec. 23, 2009.
European Patent Application No. 07763667.8 filed Feb. 5, 2007 in the name of Burnett, Office Action mailed Apr. 12, 2010.
Canadian Patent Application No. 2,620,859 filed Aug. 29, 2006 in the name of Burnett et al., Office Action mailed Apr. 20, 2010.
U.S. Appl. No. 12/351,686, filed Jan. 9, 2009 in the name of Burnett et al., non-final Office Action mailed Jul. 8, 2010.
U.S. Appl. No. 11/702,840, filed Feb. 5, 2007 in the name of Burnett et al., non-final Office Action mailed Feb. 4, 2010.
U.S. Appl. No. 10/833,950, filed Apr. 27, 2004 in the name of Burnett et al., final Office Action mailed Jan. 28, 2010.
Australian Patent Application No. 2004258968 filed Jul. 20, 2004 in the name of Baranova, Inc., Office Action mailed Feb. 10, 2011.
Australian Patent Application No. 2004258968 filed Jul. 20, 2004 in the name of Baranova, Inc., Office Action mailed Jan. 11, 2010.
Australian Patent Application No. 2005274132 filed Jul. 25, 2005 in the name of Baranova, Inc., Office Action mailed Mar. 22, 2010.
Australian Patent Application No. 2006284801 filed Aug. 29, 2006 in the name of Baranova, Inc., Office Action mailed Oct. 16, 2009.
Canadian Patent Application No. 2,534,118 filed Jul. 20, 2004 in the name of Baranova, Inc., Notice of Allowance mailed Jan. 24, 2011.
Canadian Patent Application No. 2,576,476 filed Jul. 25, 2005 in the name of Baranova, Inc., Office Action mailed Dec. 3, 2010.
Canadian Patent Application No. 2,620,859 filed Aug. 29, 2006 in the name of Baranova, Inc., Notice of Allowance mailed Feb. 4, 2011.
Japanese Patent Application No. 2006-521910 filed Jul. 20, 2004 in the name of Polymorfix, Inc., Office Action mailed Mar. 9, 2010.
U.S. Appl. No. 10/833,950, filed Apr. 27, 2004 in the name of Burnett et al., Non-final Office Action mailed Nov. 17, 2010.
U.S. Appl. No. 11/702,840, filed Feb. 5, 2007 in the name of Burnett, Final Office Action mailed Oct. 27, 2010.
U.S. Appl. No. 12/351,686, filed Jan. 9, 2009 in the name of Burnett et al., final Office Action mailed Mar. 11, 2011.
U.S. Appl. No. 12/351,705, filed Jan. 9, 2009 in the name of Burnett et al., Non-final Office Action mailed Sep. 29, 2010.
U.S. Appl. No. 12/352,497, filed Jan. 12, 2009 in the name of Burnett et al., Non-final Office Action mailed Dec. 23, 2010.
U.S. Appl. No. 11/215,430, filed Aug. 29, 2005 in the name of Burnett et al., Non-final Office Action mailed Mar. 23, 2011.
U.S. Appl. No. 12/434,594, filed May 1, 2009 in the name of Burnett et al., Non-final Office Action mailed Mar. 24, 2011.
U.S. Appl. No. 12/351,644, filed Jan. 9, 2009 in the name of Burnett et al., Non-final Office Action mailed Mar. 24, 2011.
U.S. Appl. No. 12/351,665, filed Jan. 9, 2009 in the name of Burnett et al., Non-final Office Action mailed Mar. 24, 2011.
U.S. Appl. No. 11/602,620, filed Nov. 20, 2006 in the name of Burnett, Non-final Office Action mailed Mar. 29, 2011.

(56) References Cited

OTHER PUBLICATIONS

Australian Patent Application No. 2007212404 filed Feb. 5, 2007 in the name of Baranova, Inc., Office Action mailed May 2, 2011.
U.S. Appl. No. 11/702,840, filed Feb. 5, 2007 in the name of Burnett et al., Non-final Office Action mailed May 20, 2011.
U.S. Appl. No. 12/351,705, filed Jan. 9, 2009 in the name of Burnett et al., Non-final Office Action mailed Jun. 9, 2011.
Japanese Patent Application No. 2007-525638 filed Jul. 25, 2005 in the name of Baranova, Inc., Office Action mailed Jan. 4, 2011.
European Patent Application No. 05774631.5 filed Jul. 25, 2005 in the name of Baranova, Inc., Office Action mailed Mar. 25, 2011.
Australian Patent Application No. 2007212473 filed Feb. 5, 2007 in the name of Baranova, Inc., Office Action mailed Apr. 20, 2011.
Japanese Patent Application No. 2008-529243 filed Aug. 29, 2006 in the name of Baranova, Inc., Office Action mailed May 17, 2011.

\* cited by examiner

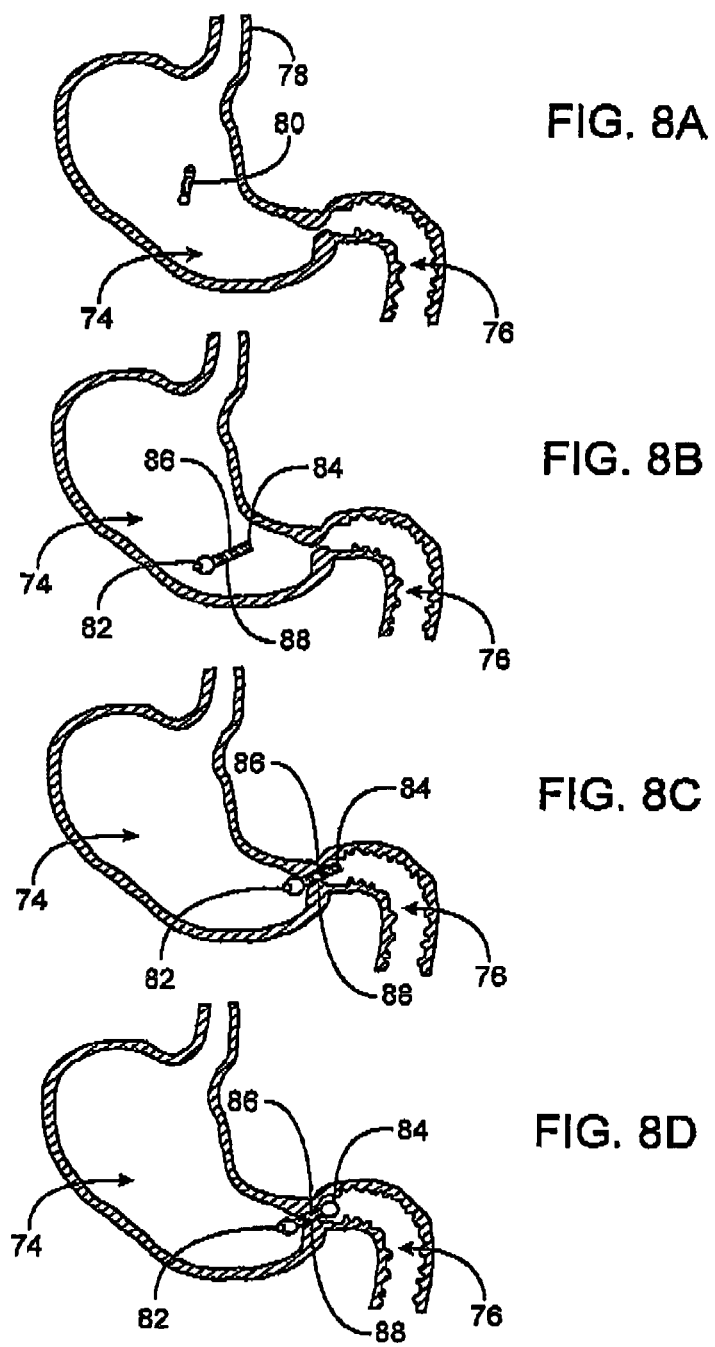

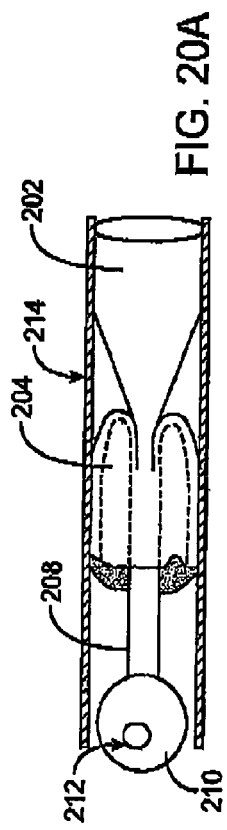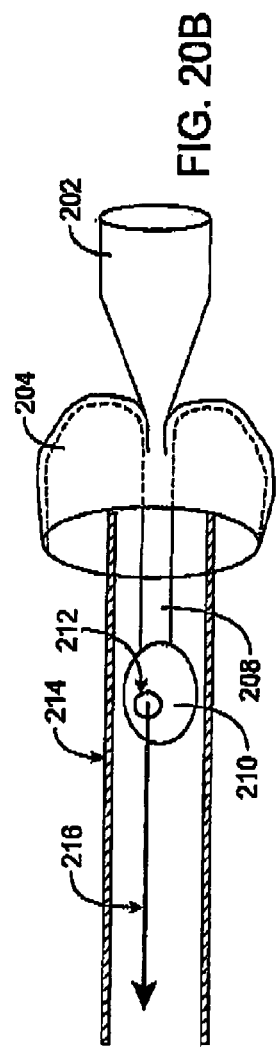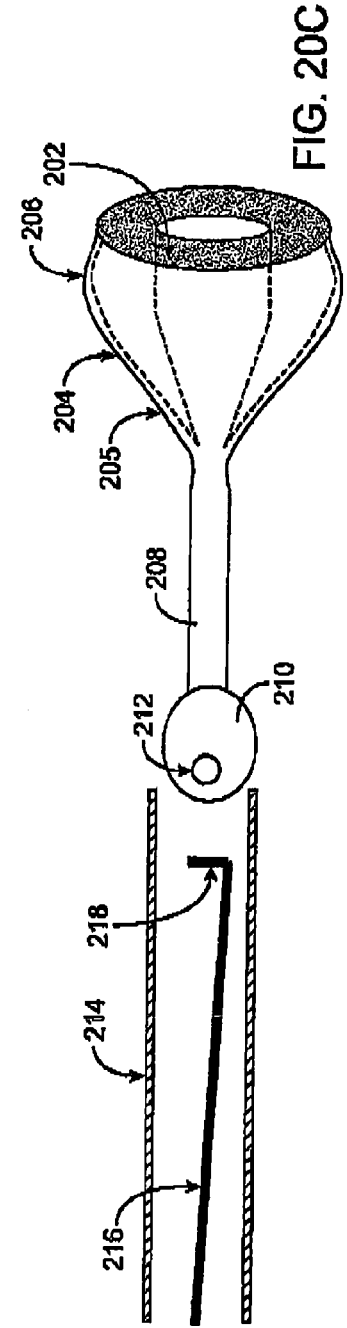

DEVICES AND METHODS FOR PYLORIC ANCHORING

CROSS-REFERENCES TO RELATED APPLICATIONS

This application is a continuation-in-part of U.S. patent application Ser. No. 10/833,950, filed Apr. 27, 2004, and entitled "Pyloric Valve Obstructing Devices and Methods,", which claims priority to U.S. patent application Ser. No. 10/671,191, filed Sep. 24, 2003, and entitled "Pyloric Valve Corking Device and Method," which claims priority to U.S. Provisional Patent Application Ser. No. 60/490,421, filed Jul. 28, 2003, and entitled "Pyloric Valve Corking Device and Method," the full disclosures of which are hereby incorporated by reference. This application also claims priority to U.S. Provisional Patent Application Ser. No. 60/525,105, filed Nov. 26, 2003, and entitled "Intragastric Therapeutic Device and Method," the full disclosure of which is hereby incorporated by reference.

BACKGROUND OF THE INVENTION

The present invention relates generally to medical devices and methods. More specifically, the invention relates to devices and methods that for performing a function in a gastrointestinal tract.

Obesity has become a medical problem of epidemic proportions in the United States. Recent governmental studies estimate that as many as 40% of Americans are obese (defined as a Body Mass Index over 30), and of those, almost 20% are morbidly obese. Unfortunately, there is no indication that these percentages will decrease and every indication that they will increase in the coming years. Studies have linked obesity to countless health risks, a small sampling of which includes cardiovascular disease, cancer, diabetes, orthopedic injuries and complaints, obstructive sleep apnea, chronic fatigue and depression. Despite billions of dollars spent searching for obesity cures, conducting research into nutrition and exercise, and educating the public about obesity, efforts to date have been largely ineffective.

Many Americans have tried combating obesity with diet, exercise and even medications, to no avail. Most people who lose weight through diet and exercise gain it back again in a short period of time. Available medications can have serious side effects, as was evidenced by the recent scare with the Fen-Phen dietary medication. Faced with the difficulty of diet and exercise, nutritional information that seems to change radically and rapidly, and diet medications and supplements that typically do not work and may cause serious side effects, many obese people become frustrated and either decide to remain obese or choose to pursue a more drastic treatment option.

The more drastic options typically involve surgical procedures, such as stomach stapling, other gastric reduction surgical techniques, placement of a constrictive band around the outside of the stomach, and gastic bypass. The most well known procedure, in part due to well-publicized experiences of celebrities like Al Roker and Carney Wilson, is the gastric bypass operation, known technically as a Roux-En-Y gastric bypass. In this procedure, the stomach is actually bypassed, and a very small stomach-like pouch remains, making a patient feel full after ingesting a small amount of food. Although gastric bypass can be highly effective, it is acknowledged to be a very high-risk operation, with a 1-2% mortality rate, a number of possible complications such as digestive problems, and a recovery period of up to 6 months. The other surgical alternatives are also associated with either high risk, low rate of effectiveness, or both.

Stemming from the high risks of gastric surgical procedures and the ineffectiveness of diet and exercise for many obese people, a number of medical devices have been developed to address weight loss and obesity, but these too have numerous drawbacks. Some devices, for example, try to bypass a portion of the stomach or small intestine by essentially creating a tube or chute through which food passes without any nutrients or calories being absorbed. Such devices are described, for example, in U.S. Pat. No. 5,820,584 and U.S. patent application Publication Nos. 2003/0040804 and 2003/0109931. Other techniques involve placing space-occupying balloons and other devices within the stomach to make the patient feel full after eating small amounts of food. One such a device, for example, is described in U.S. patent application Publication No. 2003/0109935.

One significant drawback of currently available devices such as absorption-reducing gastrointestinal sleeves and space occupying gastric balloons is that they are directly attached to the wall of the gastrointestinal tract. Such direct attachment may often lead to erosion and ulceration of the lining of the stomach or small intestine. Another significant risk with currently available devices is that if the direct attachment to gastrointestinal tissue fails for some reason, the device may pass through the pyloric valve of the stomach and into the small intestine. From there, the device may cause a blockage in the small or large intestine, which typically requires surgery and may be fatal if discovered too late.

Another approach for obesity treatment, as described, for example, in U.S. patent application Publication No. 2003/0093117, involves performing a minimally invasive surgical procedure on a stomach, typically to reduce its volume. Yet another approach involves severing or stimulating the vagus nerve in an attempt to slow the rate at which food passes from the stomach into the duodenum. Others have tried slowing gastric emptying by placing implants or injecting bulking agents into tissue at or immediately adjacent the pyloric valve. Such techniques are described, for example, in U.S. Pat. No. 6,540,789 and U.S. patent application Publication Nos. 2003/0153806 and 2003/0158601. In general, all of these types of therapies require invasive, sometimes irreversible, surgical procedures, risking a number of potential serious side effects to the functioning of the gastrointestinal tract.

Of course, obesity is not the only health problem associated with the gastrointestinal tract. It is offered here merely as an example of one serious gastrointestinal-related health problem without an ideal means of treatment or cure. Many other health conditions are caused or directly related to functioning of the gastrointestinal tract, and like obesity, many such conditions do not currently have optimal medical or surgical treatments.

Therefore, a need exists for effective, minimally-invasive or non-invasive devices and methods for obesity and other conditions related to the gastrointestinal tract. Ideally, such devices and methods would be relatively easy to use and deploy in a patient and would help treat obesity and/or other conditions without a high risk of side effects or severe complications. Ideally, such devices and methods would also be reversible and/or capable of being modified via external devices or minimally invasive means. At least some of these objectives will be met by the present invention.

BRIEF SUMMARY OF THE INVENTION

The present invention provides devices, methods and systems for performing one or more function in a gastrointestinal tract of a patient. Generally, the devices include an anchoring member and either one or more actuators, one or more sensors, or a combination of both. The anchoring member maintains the device within the pyloric portion of the patient's stomach and prevents passage of the device through the pyloric valve, but only intermittently contacts stomach wall tissue, thus avoiding erosion and ulceration of the stomach wall. In various embodiments, any of a number of actuators, sensors and/or additional components may be coupled with the anchoring member for performing various functions in the gastrointestinal tract. Anchoring devices that maintain themselves within the stomach, resisting passage through the pyloric valve while only intermittently contact stomach tissue, provide an advantageous, minimally invasive platform for administering various therapies, sensing various characteristics and/or performing other useful functions within a gastrointestinal tract.

In one aspect of the present invention, a device for performing one or more functions in a gastrointestinal tract of a patient includes an anchoring member and at least one actuator coupled with the anchoring member. The anchoring member is adapted to maintain at least part of the device within a pyloric portion of the patient's stomach and to intermittently engage, without directly attaching to, stomach tissue. The actuator(s) are adapted for performing one or more functions in the patient's gastrointestinal tract.

In some embodiments, the anchoring member comprises a stomach retention portion having sufficient size and rigidity to prevent passage of the stomach retention portion through a pyloric valve out of the stomach. In one embodiment, the actuator(s) are coupled with the stomach retention portion. In one embodiment, the stomach retention portion is expandable from a first configuration for delivery through an esophagus of the patient to a second configuration for preventing passage of the stomach retention portion through the pyloric valve. Alternatively, the device may be nonexpandable and thus adapted to be placed into the stomach via an incision in a wall of the stomach. In a number of embodiments, the anchoring member further includes a tissue engagement portion adapted to intermittently engage pyloric stomach tissue without causing significant damage to the tissue. In some embodiments, some or all of the actuator(s) are coupled with the tissue engagement portion. Such a tissue engagement portion, for example, may comprise at least one compliant material.

In some embodiments, the anchoring member further comprises a pyloric valve spanning member extending from the stomach retaining portion at least partially through a pyloric valve of the patient. Optionally, some or all of the actuator(s) may be coupled with the pyloric valve spanning member. Optionally, the anchoring member may further include a distal anchor member coupled with the pyloric valve spanning member and adapted to reside in a duodenum of the patient. One or more actuators may optionally be coupled with either the pyloric spanning member or the distal anchor member. In some embodiments, for example, the actuator is coupled with the distal anchor member and is adapted to extend into a small intestine of the patient. The distal anchor member itself may be sufficiently small to pass through the pyloric valve through natural peristalsis but sufficiently large to resist passing back into the stomach. Alternatively, the distal anchor member may be sufficiently large so as to require placement into the duodenum beyond the pyloric valve.

In some embodiments, the stomach retaining portion, the pyloric valve spanning member and/or the distal anchor member may be adapted to change configurations while residing in the gastrointestinal tract. For example, in some embodiments, the pyloric valve spanning member is adapted to change its length and/or its diameter. Such configuration changes may be triggered by receipt and processing of one or more signals by a receiver and processor of the device. For example, signals may be transmitted by one or more external or internally implanted devices adapted to transmit radiofrequency, electromagnetic, microwave or ultrasound signals. Alternatively, configuration changes may be triggered upon sensing of pH, temperature, bile content, nutrient content, fats, sugars, alcohol, opiates, drugs, analytes, electrolytes and/or hemoglobin by at least one sensor of the device.

Some embodiments of the device also include attachment means for attaching to a catheter device extended into the stomach to adjust or modify the device. For example, attachment means may include a magnet, hook or any other suitable attachment device. Such attachment means allow a device to be modified, adjusted, recharged and/or the like via a catheter placed through the esophagus, thus obviating the need for removal of the device to make adjustments.

In one embodiment, the anchoring member is adapted to intermittently obstruct the pyloric valve of the stomach, thus slowing gastric emptying. In some of these embodiments, the actuator comprises a sleeve extending within at least a portion of the small intestine to reduce absorption of nutrients by the small intestine. Optionally, such an embodiment may also include at least one tether for coupling the sleeve with the anchoring member. In one embodiment, the sleeve includes at least one proximal opening for allowing partially digested food to enter the sleeve. In some embodiments, the sleeve comprises an impermeable or semi-permeable membrane to reduce the absorption of nutrients.

In an alternative embodiment, rather than intermittently obstructing the pyloric valve, the anchoring member includes at least one passage for allowing substances to pass through the device and thus through a pyloric valve of the stomach. In such embodiments, the actuator may sometimes comprise a sleeve in fluid communication with the at least one passage for extending into a duodenum of the patient such that substances pass through the device and through the sleeve to reduce absorption of nutrients by the duodenum. In some embodiments, the sleeve extends beyond the duodenum, thus further reducing absorption of nutrients.

In some embodiments, the at least one actuator comprises at least one energy transmission member for applying energy to tissue of the gastrointestinal tract. For example, the energy transmission member may transmit energy such as but not limited to radiofrequency, ultrasound, microwave, cryogenic, laser, light, electrical, mechanical and thermal energy. In some embodiments, the energy transmission member comprises a plurality of radiofrequency electrodes adapted to apply radiofrequency energy to the stomach, the pyloric valve and/or the small intestine of the patient.

In other embodiments, the at least one actuator comprises one or more substances releasably coupled with the anchoring device. For example, such substances may include but are not limited to lipids, drugs, enzymes, diagnostic agents, lipids, vitamins, minerals and the like. In some embodiments, at least one substance is releasably coupled with an outer surface of the anchoring device such that the substance automatically releases from the surface over time. Optionally, such embodiments may further include a substrate coupled with the outer surface for releasably coupling the substance(s) with the device. In alternative embodiments, the substance(s) may be housed within at least one reservoir on the anchoring device. In some embodiments, the substance is automatically released from the at least one reservoir over time, while in alternative embodiments it is released from the reservoir(s) when the device receives a signal from a transmitter outside the patient. In some embodiments, the reservoir(s) are adapted to be refilled while the device resides in the gastrointestinal tract. For example, such reservoirs may be refilled via a catheter device passed into the stomach via the esophagus of the patient.

In some embodiments, the at least one actuator comprises at least one space-occupying member for occupying space in the stomach to enhance the patient's feeling of satiety. For example, in one embodiment the space-occupying member may comprise an expanded portion of the anchoring member. In another embodiment, the space-occupying member may be a separate piece coupled to the anchoring member via a tether.

In one embodiment, the at least one actuator comprises one or more triggers adapted to elicit a biological response. For example, the trigger may comprise a surface coating adapted to induce a satiety response. Such a surface coating, for example, may be adapted to interact with biological lipid or fat sensors in the duodenum. In some embodiments, the surface coating is adapted to elute from the device over time to induce the satiety response. Such an eluting surface coating may comprise, in one embodiment, fat, lipid, carbohydrate and/or protein derivatives. In an alternative embodiment, the trigger comprises a mechanical stimulant adapted to induce a satiety response.

In some embodiments, the at least one actuator comprises at least one imaging device. The imaging device, for example, may include but is not limited to a fiber optic device, an ultrasound device, a laser imaging device, an endoscopic device, a camera or a radiographic imaging device. In an alternative embodiment, the at least one actuator comprises a signal transmitter for transmitting a location signal for use in a global positioning system. In still other embodiments, the at least one actuator comprises a data storage device, such as for storing medical records of the patient.

Optionally, the device may further include at least one sensor coupled with the anchoring member for sensing one or more characteristics in the gastrointestinal tract. Such a sensor (or sensors) may be adapted to sense, for example, pH, temperature, bile content, nutrient content, fats, sugars, alcohol, opiates, drugs, analytes, electrolytes and/or hemoglobin. Such an embodiment may further include a processor adapted to process data related to the sensed signals and provide the processed data to the at least one actuator.

Some embodiments may further include at least one receiver for receiving signals from one or more transmitters located outside the patient or implanted in the patient. Again, such embodiments may optionally include a processor adapted to process the received signals and provide the processed data to the at least one actuator. Some embodiments further include a rechargeable power source adapted to be recharged via an external charging device located outside the patient. In other embodiments, any other suitable devices or combinations may be coupled with the anchoring member to facilitate or enhance performance of a function in the gastrointestinal tract.

In another aspect of the present invention, a device for performing one or more functions in a gastrointestinal tract of a patient includes an anchoring member and at least one sensor coupled with the anchoring member. As explained above, the anchoring member is adapted to maintain at least part of the device within a pyloric portion of the patient's stomach and to intermittently engage, without directly attaching to, stomach tissue. The sensor is adapted for sensing one or more characteristics in the patient's gastrointestinal tract. As mentioned above, such a sensor (or sensors) sense any suitable characteristic or multiple characteristics, such as but not limited to pH, temperature, bile content, nutrient content, fats, sugars, alcohol, opiates, drugs, analytes, electrolytes, hemoglobin and/or the like.

In some embodiments, the device further includes at least one actuator for performing a function in the gastrointestinal tract. Examples of actuators include, but are not limited to, any of the actuators described above, such as an energy transmission member, a substance releasably coupled with the anchoring member, an absorption-reducing intestinal sleeve, a triggering device, a space-occupying device, an imaging device, a data transmitter or a data storage device. In various embodiments, the device may also include a processor, one or more receivers and/or any other suitable features such as those described above.

In another aspect of the present invention, a system for performing a function in a gastrointestinal tract of a patient includes a gastrointestinal device and at least one transmitter. The gastrointestinal device includes an anchoring member adapted to maintain at least part of the device within a pyloric portion of the patient's stomach and to intermittently engage, without directly attaching to, stomach tissue, and at least one actuator coupled with the anchoring member for performing a function in the patient's gastrointestinal tract. The transmitter is adapted for activating and/or modulating activity of the actuator. In some embodiments, the gastrointestinal device includes one or more sensors coupled with the anchoring member, such as the sensors described above. The device may also optionally include a processor, one or more receivers and/or a rechargeable power source, as mentioned above.

In some embodiments, the at least one transmitter is adapted to be positioned outside the patient. Alternatively, one or more transmitters may be implanted within the patient. Some embodiments further include an elongate catheter device for delivering the gastrointestinal device through an esophagus of the patient. Also, some embodiments may include an elongate catheter device for coupling with the gastrointestinal device through an esophagus of the patient and recharging the actuator. Such an elongate device may be the same device used for delivery or may be a different device, according to various embodiments. In one embodiment, a magnetic end of the elongate catheter device is adapted to couple with an oppositely charged magnet on the gastrointestinal device. In some embodiments, the elongate catheter device is adapted to recharge one or more drug reservoirs on the gastrointestinal device. Alternatively, or additionally, the elongate catheter device may be adapted to recharge a power supply of the gastrointestinal device.

In yet another aspect of the present invention, a method for performing a function in a gastrointestinal tract of a patient involves delivering an anchoring device into the stomach and performing a function in the gastrointestinal tract using at least one actuator coupled with the anchoring device. The anchoring device itself may have any of the features described above. In one embodiment, delivering the anchoring device involves: advancing the anchoring device through an esophagus of the patient in a first, constrained configuration; and releasing the anchoring device to allow at least a portion of the device to expand from the first configuration to a larger second configuration. The portion of the anchoring device in the expanded second configuration is adapted to prevent passage of the anchoring device through a pyloric valve of the patient. Alternatively, delivering the anchoring device may involve passing the device through an incision in a wall of the patient's stomach.

In various embodiments, performing the function in the gastrointestinal tract may involve, but is not limited to, transmitting energy, releasing a substance, reducing absorption of a small intestine, stimulating gastrointestinal tissue to evoke a response, occupying space within the stomach, taking one or more images, transmitting data, storing data and/or the like. In some embodiments, the method further involves sensing at least one patient characteristic using at least one sensing device coupled with the anchoring device. The at least one sensed characteristic may include any of those listed above or any other suitable characteristic, including pH, temperature, bile content, nutrient content, fats, sugars, alcohol, opiates, drugs, analytes, electrolytes, hemoglobin and/or the like.

In some embodiments, the method may also include transmitting data to the anchoring device via at least one transmitter and receiving the transmitted data via a receiver coupled with the anchoring device. Such transmitting may be performed via one or more transmitters located outside the patient, implanted in the patient or a combination of both. Some embodiments also include processing the transmitted data via a processor coupled with the anchoring member. Optionally, the method may also include recharging the actuator while the gastrointestinal device remains within the patient. In one embodiment, recharging the actuator is performed via an external charging device located outside the patient. Alternatively, recharging the actuator may be performed via a catheter device passed into the patient's stomach via the patient's esophagus. In one embodiment, recharging the actuator involves refilling at least one drug reservoir of the gastrointestinal device. The method may optionally also involve recharging a power source coupled with the anchoring member.

In some embodiments, the anchoring member is adapted to intermittently obstruct the pyloric valve of the patient's gastrointestinal tract, thus slowing passage of food through the valve. In alternative embodiments, the anchoring member extends across a pyloric valve of the patient's gastrointestinal tract, and the anchoring member is adapted to allow passage of food therethrough, thus reducing absorption of nutrients in at least part of the patient's duodenum.

In another aspect of the invention, a method for sensing one or more patient characteristic in a gastrointestinal tract of a patient involves delivering an anchoring device into the stomach and sensing one or more patient characteristics in the gastrointestinal tract using at least one sensing device coupled with the anchoring device. Such a method may further include performing a function in the gastrointestinal tract using one or more actuators coupled with the anchoring device. Various embodiments of the method may include any of the features described above.

These and other aspects and embodiments of the invention are described in greater detail below, with reference to the attached drawing figures.

BRIEF DESCRIPTION OF THE DRAWINGS

FIGS. 8A to 8D show cross-sectional views of the stomach and yet another variation for placement of a variation of the device through ingestion.

FIGS. 20A to 20C illustrate a method for delivering and deploying the device of FIGS. 19A and 19B.

DETAILED DESCRIPTION OF THE INVENTION

Much of the following description focuses on embodiments which provide intermittent obstruction of a pyloric valve to help treat obesity. Much of the description also focuses on embodiments that expand from a smaller configuration for delivery through the esophagus to a larger configuration to assure retention of the device within the stomach. In alternative embodiments, however, devices may not, in fact, obstruct the pyloric valve, but may instead act as a conduit allowing food to pass through the pyloric valve and in some cases to reduce absorption of nutrients in the small intestine. Also, some embodiments may be adapted for placement via a surgical procedure involving an incision in the stomach wall, and thus the invention is not limited to an expanding device delivered through the esophagus. Thus, the description that follows is provided primarily for exemplary purposes, and no one embodiment should be interpreted to limit the scope of the invention as a whole.

According to various embodiments, any of a number of suitable actuators, sensors, transmitters, receivers, processors and/or the like may be coupled with any of the devices described below. Furthermore, such actuators, sensors and the like may be coupled with any suitable part of a device, such as a portion of a device adapted to reside in the stomach, another portion adapted to span the pyloric valve, a portion adapted to reside just beyond the pyloric valve in the duodenum, or some combination thereof. Many of the devices described below, such as a pyloric corking device, will thus act as an anchoring device for actuators, sensors and/or the like. Such actuators and sensors are described in more detail below.

Figure 1A:
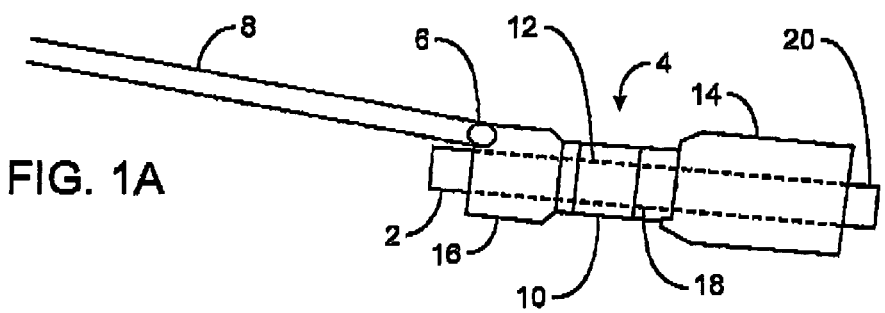
FIGS. 1A to 1C show cross-sectional views of one variation of a pyloric corking device designed to partially and/or intermittently obstruct a gastric opening in an unexpanded, partially unexpanded, and fully expanded configuration, respectively.
Figure 1B:
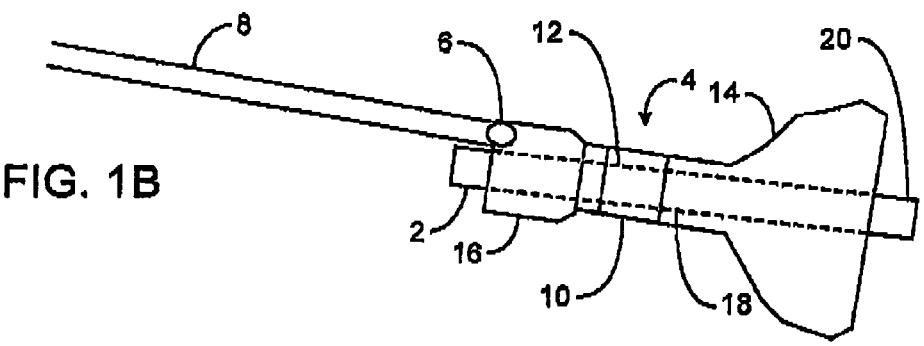
Figure 1C:
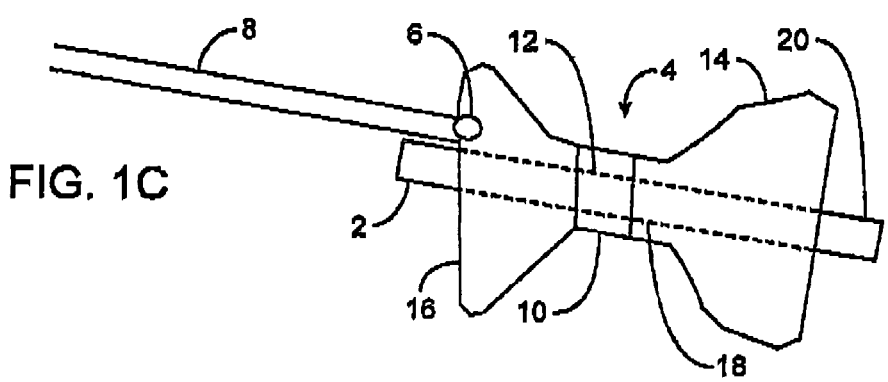

FIGS. 1A to 1C are cross-sectional views showing the expansion, respectively, of one variation of a pyloric corking device 4 which is designed to partially and/or intermittently obstruct a gastric opening, particularly the pyloric valve. In this particular variation, FIG. 1A illustrates the device 4 in an unexpanded or uninflated state and ready for delivery and/or insertion into the pyloric valve. FIG. 1B shows the distal occlusion member 14 in an expanded state. In use, once the device 4 has been placed, e.g., in the pyloric region or beyond, the distal occlusion member 14 (or "retaining member") may be inflated through the influx of any number of biocompatible fluids or gases, e.g., saline, water, air, nitrogen, etc., through the tubing 8 leading to the inflation port 6, which may be self-sealing. Tubing 8 may include any number of delivery tubes such as catheters, endoscopes, etc.

The distal occlusion member 14 may be configured to inflate before the inflation of proximal occlusion member 16 by fabricating the inflatable member of distal occlusion member 14 with a material which is more easily distensible relative to a material of the proximal occlusion member 16. Materials which may be used in fabricating the occlusion members 14, 16 may include any number of materials such as silicone, silicone elastomers, latex, polyurethane, PTFE, FEP, etc. Alternatively, self-expanding materials, such as foam or hydrogels which typically expand upon contact with fluids, may be utilized within the occlusion members 14, 16. If such self-expanding materials are utilized, they may be disposed in the occlusion member 14, 16 and a fluid such as saline, may be infused to expand the materials. Different self-expanding materials may be incorporated in the distal occlusion member 14 than in the proximal occlusion member 16 to obtain differing radial pressures exerted by the expanding materials.

In yet another alternative, an expanding scaffolding may be utilized within each of the occlusion members 14, 16. Such a scaffold may be made of a shape memory alloy or super-elastic alloy, such as Nitinol. The scaffold may be compressed into a delivery configuration and then either allowed to expand into the desired occlusive shape by self-expansion or by supplying an activation energy, e.g., electrical, heat, RF energy, etc. In either case, the distal occlusive member 14 may be positioned distal of the pyloric valve and then inflated or expanded into its larger configuration. It may then be pulled proximally against the pyloric annulus, at which point proximal occlusive member 16 may be inflated or expanded by infusion through port 6, as shown in FIG. 1C. With both occlusion members 14, 16 inflated or expanded, bridging member 10 connecting the two may span the pylorus. Bridging member 10 may be of various diameters, such as 1 mm and less, which does not significantly obstruct the pyloric sphincter, up to 8-10 mm in diameter, which does typically obstruct the pyloric sphincter, or any other suitable diameter.

Bridging member 10 may be designed to have a flexible length sufficient to allow the occlusion members 14, 16 to maintain its position with respect to the pyloric valve yet still enable the members 14, 16 to move. Proximal occlusion member 16 may move from fully obstructing the pyloric valve to moving proximally of the pyloric valve to the extent that distal occlusion member 14 allows member 16 to move. This movement may be elicited by the natural movements of the gastric lumen (stomach) and muscles surrounding the pyloric valve. Thus, when proximal occlusion member 16 is moved proximally, the pyloric valve is only partially obstructed and may allow for the intermittent passage of food between the bridging member 10 and the valve. Because any food within the stomach is retained for longer periods of time, feelings of satiation may be initiated sooner and prolonged so that the patient consumes less food. Moreover, to allow for the relative movement of the occlusion members 14, 16, bridging member 10 may be of a length which is sufficient to allow for its placement through the pyloric valve (or through another gastric opening) such that there is sufficient tolerance for the occlusion members 14, 16 to move proximally and distally relative to the pyloric valve. For instance, in the event that a patient's pyloric valve extends about 2 cm in length, the bridging member 10 is preferably longer than 2 cm, for example, up to 8 cm in length. Moreover, while occlusion members 14, 16 are inflatable or expandable, bridging member 10 itself may be configured to inflate or expand in diameter.

A visible dye or marker, preferably being highly visible, may optionally be infused into one or both of the occlusion members 14, 16 to function as a safety measure. Alternatively, one or both of the occlusion members 14, 16 may optionally be fabricated from a material which is highly visible and visually distinct from tissue so that in the unlikely event of an occlusion member 14, 16 rupturing, the dye or pieces of the occlusion member 14, 16 may become visible once passed from the body. This may indicate to the patient or physician that a rupture of the device has occurred.

Another variation may incorporate slow-releasing drugs infused into the materials covering the device or materials incorporated into the device. These drugs, which may be any number of drugs, may slowly infuse into the patient by drug release into the intestinal tract or through contact with the patient. Alternatively, the devices may incorporate electrical stimulation technologies. For instance, electrical probes may extend from a surface of the device for insertion into the surrounding tissue or electrodes may be formed over a surface of the device instead.

In yet another alternative, the occlusion members 14, 16 may be covered by an erodable or biodegradable covering over one or both members 14, 16. Such a covering may be configured to constrain one or both members 14, 16 and once the device has been ingested or placed within the gastric lumen, contact with the surrounding fluids may naturally erode the covering thus allowing the covered occlusion member to expand or inflate. In another variation, proximal and distal occlusion members may each be covered by different materials each configured to erode at differing rates or in different environments, as described in further detail below.

In the variation shown in FIGS. 1A to 1C, the device 4 may include an optional lumen 18 defined through the device 4. Optional lumen 18 may allow for the passage of fluids and food through the device 4 entering the lumen 18 through entry port 2 and exiting through the exit port 20. The lumen 18 may be designed to allow for the passage of a reduced volume of food through the device 4, in which case the device 4 shown may be configured with a relatively shortened bridging member 10 to inhibit the relative movement of the device 4 relative to the pylorus. With this variation, the lumen 18 has been configured so that it may be capable of actively pumping or metering the contents of the gastric lumen 74 into the intestine 76 through the device 4. In such a case, the need for the device 4 to be able to move to un-occlude the pyloric valve is removed. As shown in the figures, an optional pump or active metering valve 12 may be incorporated into the device 4. Pump or valve 12 may be configured to simply open and allow for the passage of the stomach contents through lumen 18 and valve 12 upon sensing the presence of foreign objects, such as food, in the stomach or upon sensing a predetermined pressure from the contents. Other sensing parameters may include temperature and pH levels. Alternatively, the pump or valve 12 may be configured to actively pump the stomach contents through the lumen 18 via a pumping mechanism automatically activated by pump or valve 12 or externally activated by the patient or physician through wireless communication. In the case where the device is configured with a valve 12, the valve may be configured as a unidirectional valve to allow the flow of fluids and food only from the stomach to the intestinal tract.

Figure 2A:
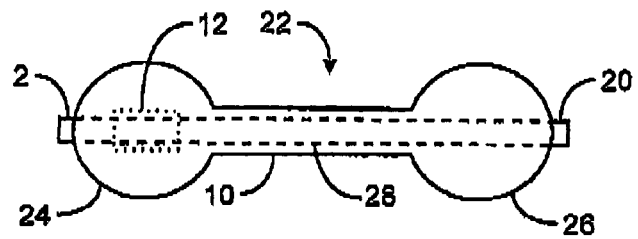
FIGS. 2A to 2D show side views of variations of the device utilizing occlusion members of different shapes.

The device 4 could have any shape provided that the shape and/or total volume of the proximal occlusion member 16 is sufficient to prevent its passage through the pyloric valve and into the intestines. FIGS. 2A to 2D show side views of different shape variations which are possible for use as occlusion members. For instance, FIG. 2A shows a side view of a device variation 22 in which proximal and distal occlusion members 24, 26 have a cross-sectional shape along a longitudinal axis defined by the device 22 in the form of circles, to form spherical occlusion members. Although proximal and distal occlusion members 24, 26 are illustrated having equally sized diameters, the diameters may be varied depending upon the desired shape and device configuration. For instance, proximal occlusion member 24 may be configured to have a diameter larger than distal occlusion member 26. Alternatively, a device having the opposite configuration may also be utilized, although this may be less preferable. Lumen 28 and pump or valve 12 may be optionally included, again depending upon the desired device configuration.

Figure 2B:
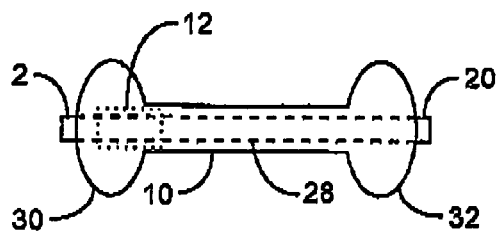
Figure 2C:
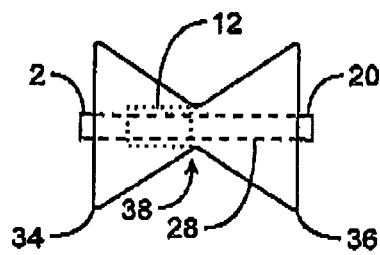
Figure 2D:
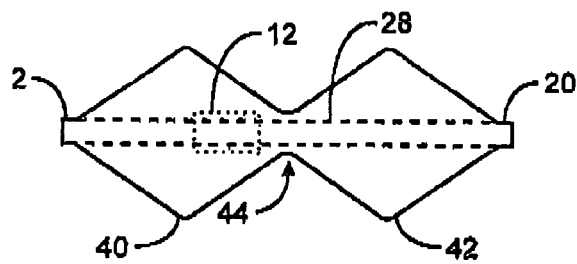

FIG. 2B shows another device variation in which proximal and distal occlusion members 30, 32 may have a cross-sectional shape along a longitudinal axis defined by the device in the form of ellipses, to form ellipsoids. The major axes of the elliptically-shaped occlusion members 30, 32 are preferably oriented perpendicularly relative to the longitudinal axis of the device in this variation, although various angles may be formed as well. FIG. 2C shows the variation in which proximal and distal occlusion members 34, 36 may be formed as triangles, to form conically-shaped occlusion members. In this variation, bridging member 38 may be minimal in length and may simply be formed by the intersection of the occlusion members 34, 38 to form a waist region. FIG. 2D shows yet another variation in which proximal and distal occlusion members 40, 42 may be formed as diamond shapes, to form a variation of conically-shaped occlusion members. This variation may also form a waist region 44.

Although these variations show specific shapes, these are merely intended to be illustrative of the various types of shapes which may be utilized and is not intended to be limiting. For instance, any shape, such as rectangles, squares, etc., which may function to occlude a gastric opening and prevent the device from falling therethrough may be utilized and are within the scope of this disclosure. Moreover, various combinations of the different shapes as occlusion members on a single device may also be utilized, such as a device having a distal occlusion member in the shape of a sphere and a proximal occlusion member in the shape of a cone.

Figure 3A:
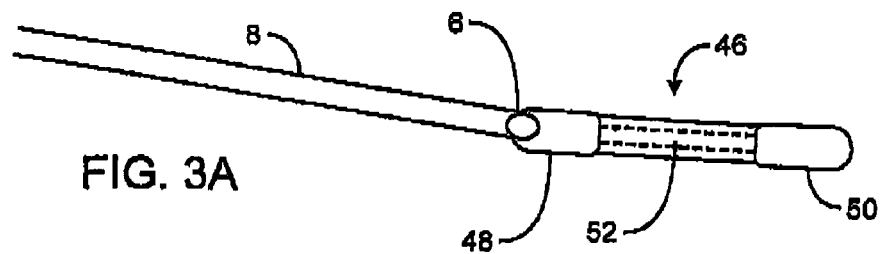
FIGS. 3A to 3C show cross-sectional views of another variation of the pyloric corking device.
Figure 3B:
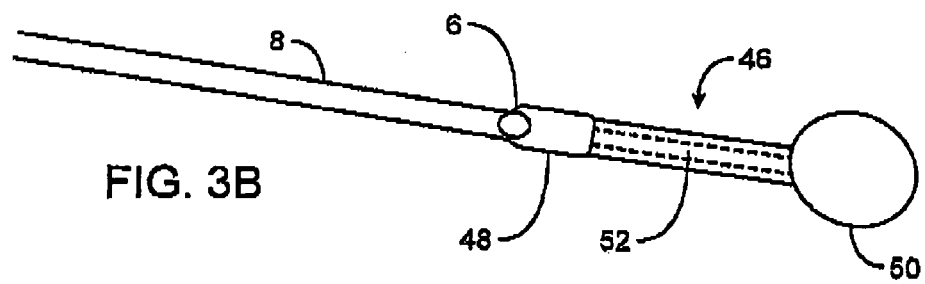
Figure 3C:
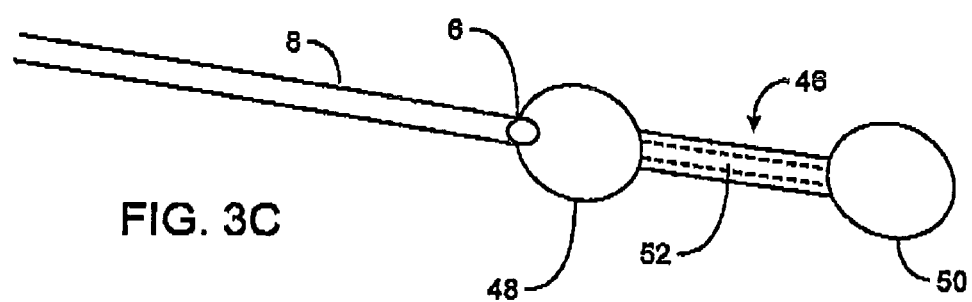

FIGS. 3A to 3C show cross-sectional views of another variation of a pyloric corking device which is also designed to intermittently obstruct a gastric opening. Similar to the device shown in FIGS. 1A to 1C, this particular variation omits the use of a lumen defined through the entire device 46. This device 46 may also incorporate any of the features described above for expanding the occlusion members. For instance, foam of varying expansion pressures may be utilized to ensure that expansion occurs in the distal occlusion member 50 prior to expansion in the proximal occlusion member 48 upon the injection of a fluid, e.g., saline or water, into the device 46. The device 46 is configured so that the influx of fluids from the infusion tubing 8 through the entry port 6 is channeled through the lumen 52 of the central portion from the proximal occlusion member 48 to the distal occlusion member 50. The device 46 may also be placed in the same manner as a device as in FIGS. 1A to 1C, as described in further detail below. This variation may also incorporate an inflation port 6, which may be metallic, so that removal of the device 46, if necessary, can be accomplished through the simple placement of a magnetically tipped suction catheter. The catheter, when appropriately placed, may cause the device to deflate by applying a suction force to facilitate the easy removal of the device 46 from the pyloric valve. The device 46 can thus be removed through any endoscopic or percutaneous approach, e.g., an oro- or naso-gastric approach. While this variation may have a lumen 52 connecting the proximal 48 and distal 50 occlusion members, this lumen 52 may be closed to gastric space and instead be used to communicate an inflation fluid to inflate the occlusion members 48, 50. The occlusion members of the device 46 may have any shape as described above, for instance in FIGS. 1A to 2D.

Figure 4A:
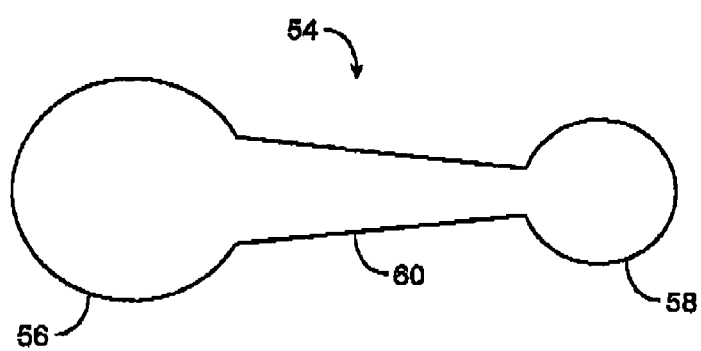
FIG. 4A shows a side view of yet another variation of the device having a tapered bridging member.

Yet another variation of the device is shown in FIG. 4A. In this variation, the device 54 may have a bridging member 60 which is tapered. The bridging member 60 may be tapered to become wider along its length from the distal occlusion member 58 to the proximal occlusion member 56. The tapered bridging member 60 may be utilized to facilitate movement of the device 54 to un-occlude the pyloric valve. As the pyloric valve contracts about the bridging member 60, the taper may aid in moving the device proximally. The angle of the taper may be varied, depending upon the desired results, as may the size and shapes of the occluding members 56, 58.

Figure 4B:
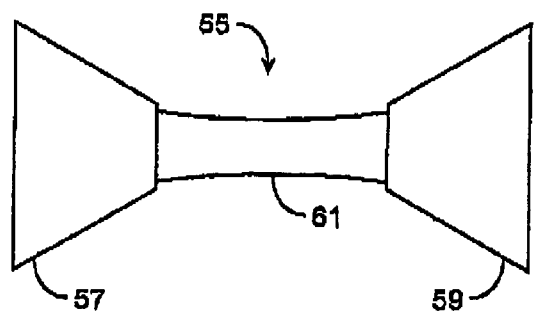
FIG. 4B shows a side view of yet another variation of the device having conical occlusion members held at a distance from one another.

FIG. 4B shows another variation similar to that shown above. In this variation, the device 55 may have occlusion members 57, 59 having conically-shaped members which are connected via a bridging member 61. This bridging member 61 may have a length which holds occlusion members 57, 59 at a distance from one another sufficient to enable the device 55 to move relative to the pyloric valve. The device 55 may inflate or expand the occlusion members 57, 59 using any of the methods disclosed herein and the device 55 may also optionally incorporate a central lumen and a passive or active valve or pumping mechanism, if desired.

Figure 5A:
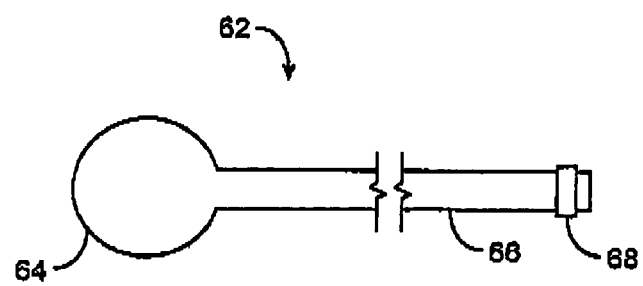
FIGS. 5A and 5B show side views of yet another variation of the device having a single occlusion member and alternative anchor members.
Figure 5B:
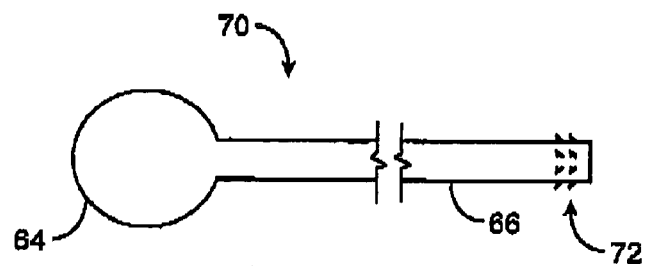

In another embodiment, the distal occlusion member may be omitted entirely. FIG. 5A, for instance, shows a side view of an alternative variation 62 in which the bridging member 66 (or "positioning member") may extend at some length, e.g., 5 cm or greater, from a proximal occlusion member 64. The bridging member 66 may be placed within the intestinal tract, e.g., the duodenum, while held in place by the proximal occlusion member 64 abutting the pyloric valve. The positioning of the proximal occlusion member 64 relative to the pyloric valve may be maintained by the frictional forces generated by the bridging member 66 rubbing against the walls the intestinal tract. The occlusion member 64 may function in the same manner as described above in intermittently un-occluding the pyloric valve during stomach contractions and movement, but may be held in place by the length of the bridging member 66. Although the distal end of the bridging member 68 may be free-floating in the intestinal tract, it may optionally be weighted by a weight 68 or by a number of hooks or barbs 72 for attachment to the intestinal walls, as shown in the device 70 of FIG. 5B.

It is furthermore within the scope of this disclosure that certain features between the different device variations described herein may be incorporated into various combinations. For instance, a device having a proximal occlusion member having a spherical shape and a distal occlusion member having a conical shape may be utilized. As a further example, this device may also incorporate various methods to inflate or expand the distal occlusion member in a different manner as the proximal occlusion member. Moreover, this device may also have a biodegradable covering over only one occlusion member and may also incorporate the valve and/or pump integrated within the device and may also optionally include a lumen defined throughout the length of the device. These examples are merely intended to be illustrative of the various combinations which may be employed by combining various aspects from different variations described herein and are intended to be within the scope of this invention.

Figure 6A:
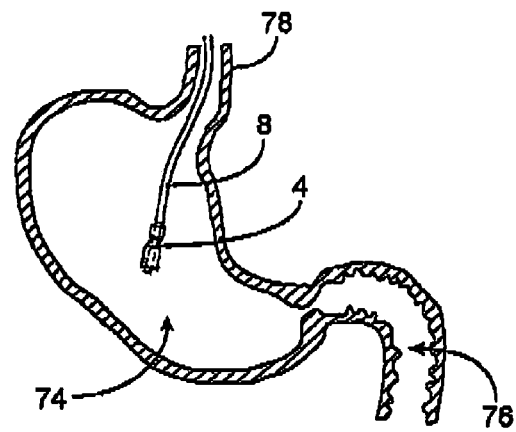
FIGS. 6A to 6C show cross-sectional views of the stomach and one variation for nasogastric (or endoscopic) placement of a non-ingestible variation of the device.
Figure 6B:
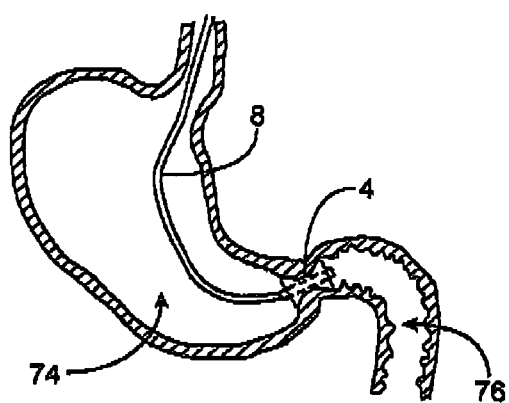
Figure 6C:
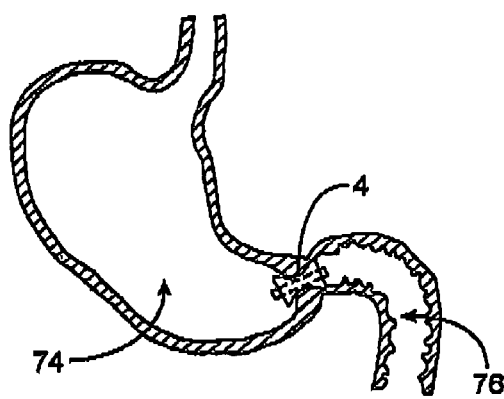

FIGS. 6A to 6C show cross-sectional views of the stomach and one variation for nasogastric (or endoscopic) placement of a non-ingestible, active variation of the device 4. As the device 4 is delivered through the esophagus 78, it may be in a compressed, un-inflated, or un-expanded configuration, as shown in FIG. 6A, while being positioned via the optional tubing 8. Once the device 4 has been positioned to span the pylorus with the occlusion members in the stomach 74 and duodenum 76, respectively, the device 4 may be inflated or expanded using any of the methods described above, as shown in FIG. 6B. The tubing 8 may then be detached and the device 4 left in place, as shown in FIG. 6C.

Figure 7A:
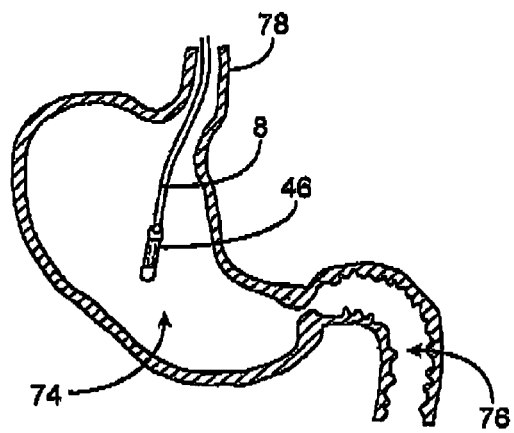
FIGS. 7A to 7C show cross-sectional views of the stomach and another variation for nasogastric (or endoscopic) placement of a non-ingestible variation of the device.
Figure 7B:
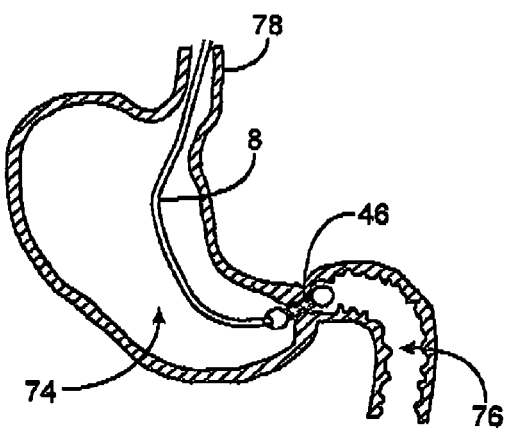
Figure 7C:
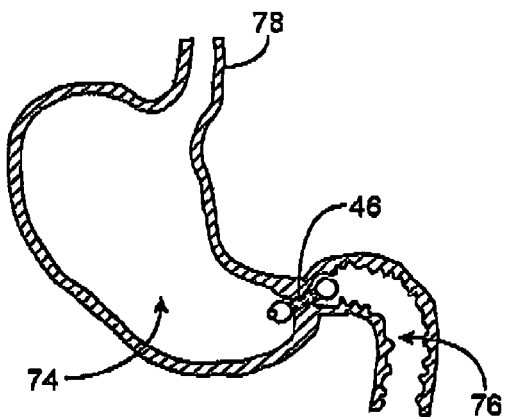

FIGS. 7A to 7C show cross-sectional views of the stomach and another variation for nasogastric (or endoscopic) placement of a non-ingestible, passive variation of the device 46. As above, the device 46 may be advanced through the esophagus 78 while in a compressed, un-inflated, or un-expanded configuration, as shown in FIG. 7A. As shown in FIG. 7B, once the device 46 has been placed spanning the pylorus with the occlusion members in the stomach 74 and duodenum 76, respectively, the device may be inflated or expanded and the tubing 8 may be detached and the device 46 left in place, as shown in FIG. 7C.

FIGS. 8A to 8D show cross-sectional views of the stomach and yet another variation for placement of a passive (or "self-expanding") embodiment of the device 80. As shown in FIG. 8A, the device 80 may be simply ingested. As it enters the stomach 74, gastric fluids may erode an acid sensitive coating over the inflation port of the proximal occlusion member 82. Once the coating has degraded, the proximal occlusion member 82 may be configured to expand or inflate, as shown in FIG. 8B. Once the expansion or inflation has occurred, the device 80 will remain in the stomach 74 and eventually the distal occlusion member 84 may pass into the duodenum 76 while still in its un-expanded or un-inflated state due to the natural contractions of the stomach, as shown in FIG. 8C. Once the distal occlusion member 84 has passed into the duodenum 76, an alkaline sensitive coating over the distal occlusion member 84 may be eroded and expansion or inflation of the distal occlusion member 84 will occur with the device spanning the pyloric valve, as shown in FIG. 8D. The covering over the distal occlusion member 84 may be configured to erode only once it has contacted the acidic environment specific to the duodenum 76, where the pH level is approximately 6. In order to facilitate removal, the two occlusion members 82, 84 may be connected by a central, hollow lumen 86, as described above, with a barrier 88 designed to rupture upon the application of a predetermined pressure level. Thus, with application of a vacuum having the appropriate pressure level, the barrier 88 may be configured to rupture and the entire device 80 may be deflated.

Figure 9A:
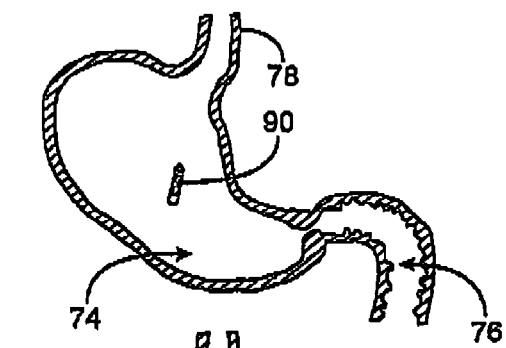
FIGS. 9A to 9D show cross-sectional views of the stomach and yet another variation for placement of another variation of the device through ingestion.
Figure 9B:
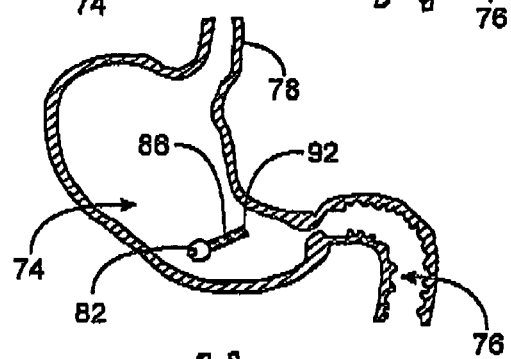
Figure 9C:
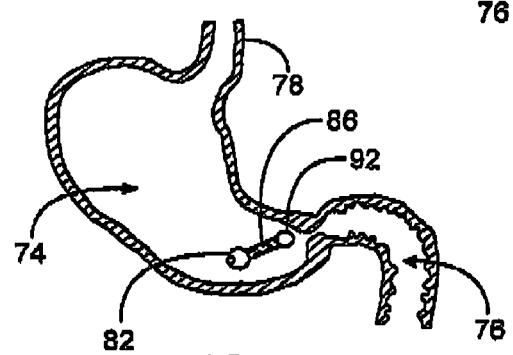
Figure 9D:
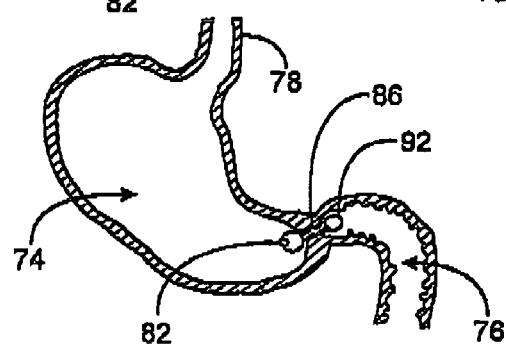

FIGS. 9A to 9D show cross-sectional views of the stomach and yet another variation for placement of a passive variation of the device 90 through ingestion. In this alternative variation, the device 90 can be ingested orally. As the device 90 enters the stomach 74, shown in FIG. 9A, both the proximal and distal occlusion members 82, 92, respectively, may be configured to inflate upon erosion of acid-sensitive coatings over the inflation port or device 90, as shown in FIGS. 9B and 9C. Once inflation or expansion has been accomplished, the distal occlusion member 92 will eventually be passed due to its smaller size (approximately the diameter of the dilated pyloric valve 5-15 mm) while the proximal occlusion member 82 will remain in the stomach 74 due to its larger size, e.g., 15 mm or greater in diameter and up to 60 mm in diameter due to physiologic limitations in the pyloric region of the stomach, as shown in FIG. 9D. Thus, one occlusion member 92 may be designed to be small enough to be passed through the pyloric valve while the proximal occlusion member 82 may be designed to be retained in the stomach 74 with both occlusion members 82, 92 inflating in the stomach 74.

A number of different alternatives and variations may be employed in self-expanding or "passive" pyloric valve obstructing devices and methods such as those just described. In some embodiments, a device may be folded, compressed or otherwise formed into a smaller configuration for swallowing by a patient, without using a biodegradable coating. Upon passing through the esophagus into the stomach, the folded device may unfold due to one or more shape-memory Nitinol support rings or other self-expanding support members. In any swallowing embodiment, a device may also include a tether that extends from the device, back through the esophagus to the patient's mouth. Such a tether may be used for retaining the obstructing device in the stomach until it expands, retrieving the obstructing device if it does not deploy as desired in the patient's stomach and/or the like. In some embodiments, the tether may be swallowed to dissolve in the stomach. In other embodiments, a swallowed device may contact the pyloric valve but not include a bridging member for spanning the valve. Other variations are contemplated within the scope of the invention, according to various embodiments.

Figures 10A, 10B, 10C, 10D:
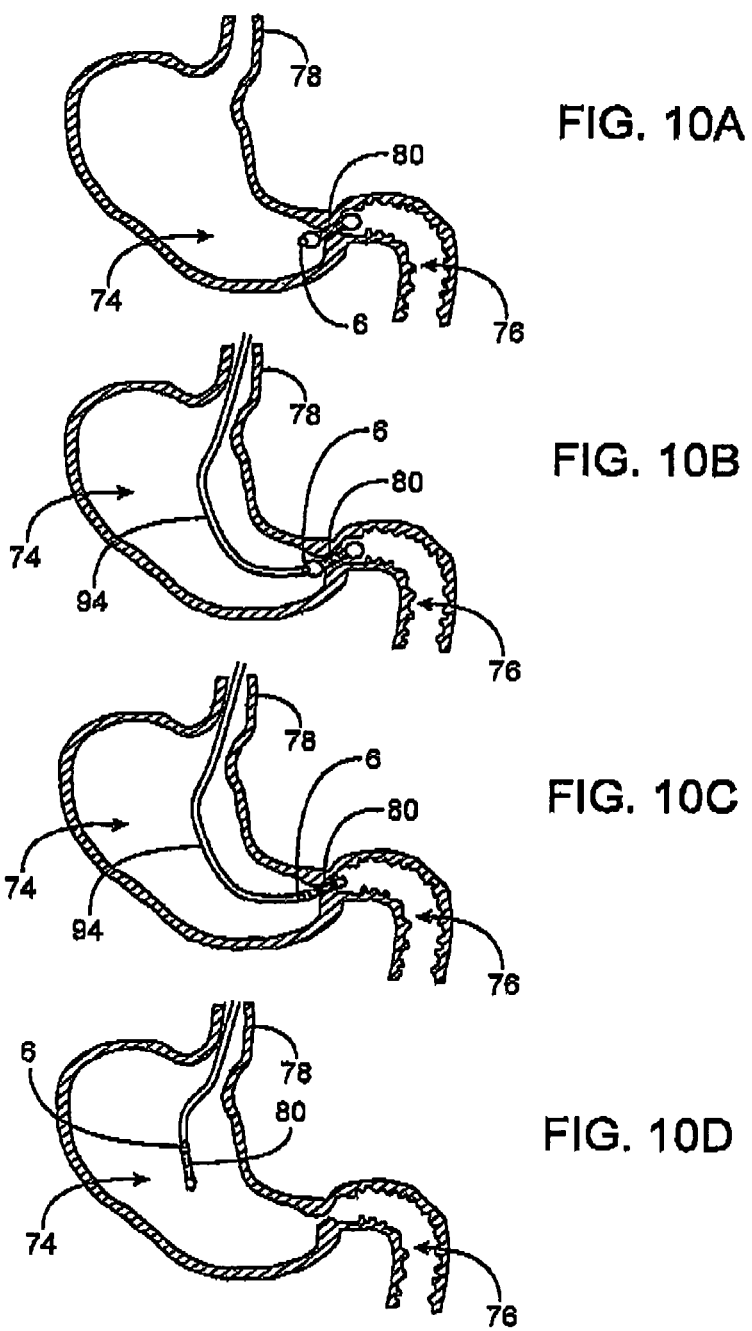
FIGS. 10A to 10D show cross-sectional views of the stomach and one variation for removal of the device.

FIGS. 10A to 10D show cross-sectional views of the stomach 74 showing one variation for removal of the device 80 (passive variation illustrated). The device 80 is shown in FIG. 10A between the stomach 74 and the duodenum 76. As seen in FIG. 10B, a magnetic tipped suction catheter or endoscope 94 is introduced and the device 80 may be deflated and removed, as shown in FIGS. 10C and 10D. In contacting the inflation port 6 with the catheter 94, the tip may be configured with an electrical contact as an aid in determining whether the catheter 94 has properly contacted the inflation port 6. Alternatively, the device 80 may be removed through endoscopy or it may be designed to degrade over time and eventually be passed through the intestines.

In other embodiments, an obstruction device may be removed by deflating or collapsing the device and removing it through a lumen of a catheter device. In one embodiment, the device may be cut into small pieces and removed through a catheter lumen in yet another embodiment, the device may dissolve over time and pass harmlessly through the pyloric valve and the digestive system. Any number of suitable alternatives for removal or passage of the device are possible in various embodiments.

Figure 11A:
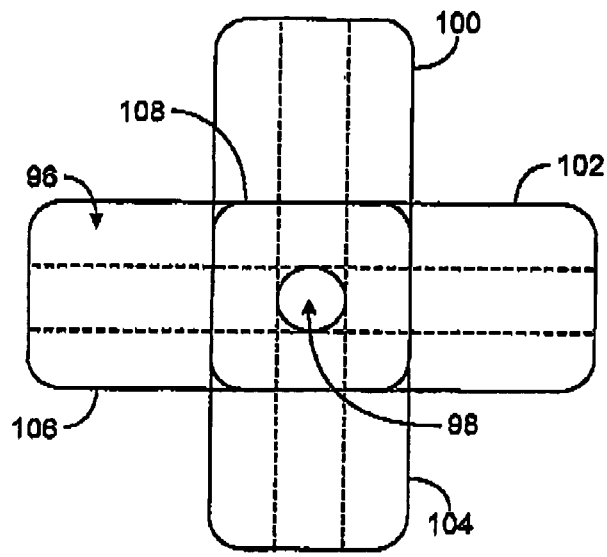
FIGS. 11A and 11B show top and perspective views, respectively, of an alternative variation of the device incorporating multiple prongs designed to intermittently obstruct the pyloric valve.
Figure 11B:
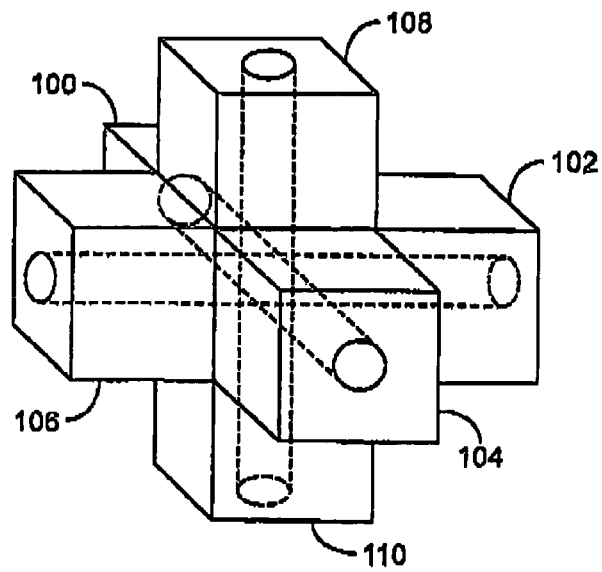

FIGS. 11A and 11B show top and perspective views, respectively, of an alternative variation for the device which may reside solely in the stomach. This particular variation may incorporate multiple prongs 100, 102, 104, 106, 108, 110 designed to intermittently cork the pylorus. In this variation, an expansile material 96 may be appropriately shaped in order to promote occlusion of the pylorus. The device may be ejected from the pylorus due to contractions, but may be re-inserted through one of the various prongs. As a further measure, the device may define multiple apertures 98 through each set of prongs to prevent complete obstruction of the pyloric valve.

Figure 12A:
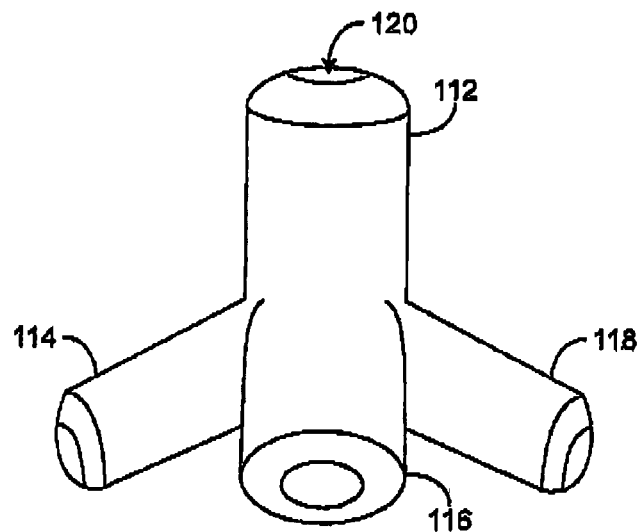
FIGS. 12A and 12B show side and top views, respectively, of another variation of the device incorporating multiple prongs designed to intermittently obstruct the pyloric valve.
Figure 12B:
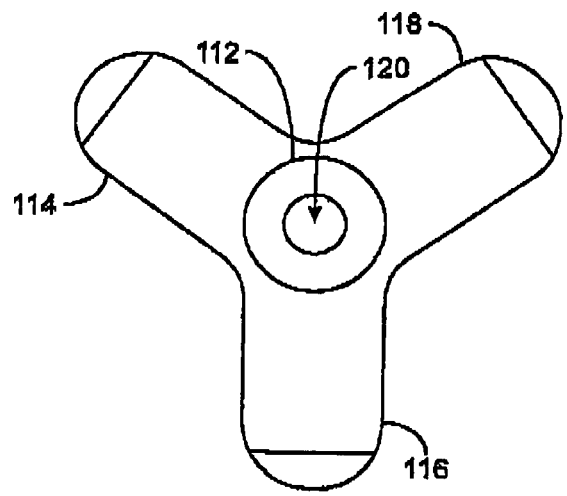
Figure 13A:
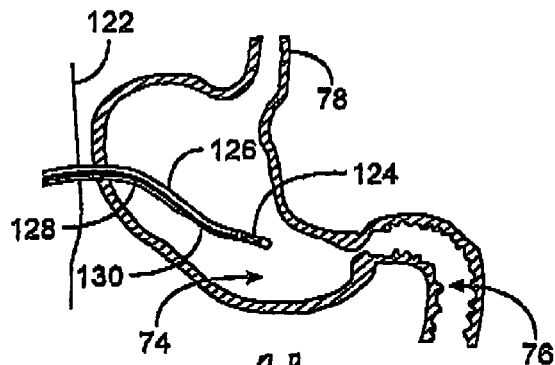
FIGS. 13A to 13D show cross-sectional views of an alternative use of the device for preventing gastroduodenal reflux during tube feeding.
Figure 13B:
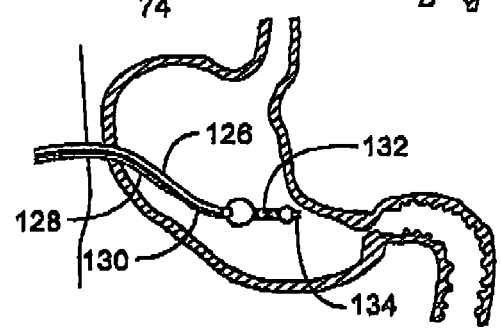
Figure 13C:
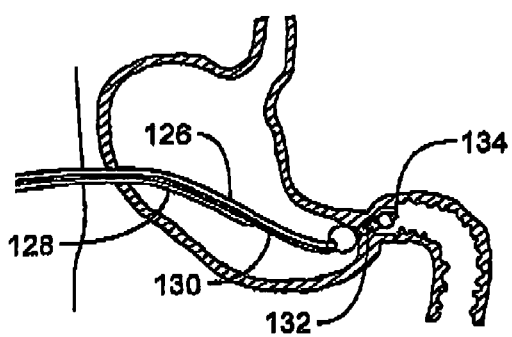
Figure 13D:
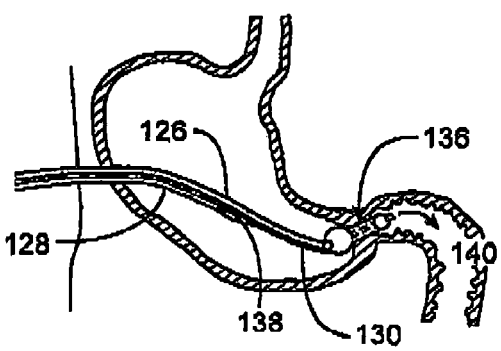

FIGS. 12A and 12B show side and top views, respectively, of another variation of A device as in FIGS. 11A and 11B. In this variation, a fewer number of multiple prongs 112, 114, 116, 118 may be utilized and each prong may also define an aperture 120 therethrough. However, as shown in this variation, each of the prongs may be flexible and tapered or rounded to prevent damage to the surrounding tissue.

FIGS. 13A to 13D show cross-sectional views of an alternative use of the devices described herein. In this variation, the device may be utilized in the prevention of gastroduodenal reflux during tube feeding. As shown, the device 124 is similar to variations described above; however, in this variation, a lumen 132 defined through the device 124 for tube feed delivery may define an outlet 134 designed to be positioned in the duodenum 76. The proximal portion of the device 124 may also be attached to a feeding tube 126 and an inflation tubing 130. Feeding tube 126 may be used to deliver tube feeds through the lumen 132 directly to the duodenum 140 while the inflation tubing 130 may be used to inflate an inflatable pyloric spanner or bridging member 136 during tube feeding to prevent reflux of delivered material 140. The device 124 can also incorporate a third tube 128 which may provide for aspiration of the gastric contents 138 to prevent reflux of the delivered material into the lungs and to decompress the stomach 74. The proximal portion of the occlusive member can either maintain its inflated or expanded state or it can be decompressed at times to relieve pressure on the pyloric valve. In this variation, a percutaneous approach is shown, but a nasogastric approach or another approach is possible.

Figure 14A:
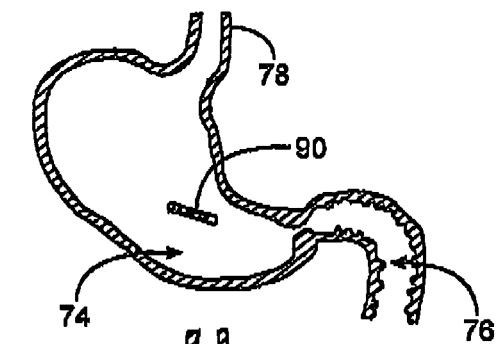
FIGS. 14A to 14D show cross-sectional views of an alternative use of the device in combination with one or several gastric fillers.
Figure 14B:
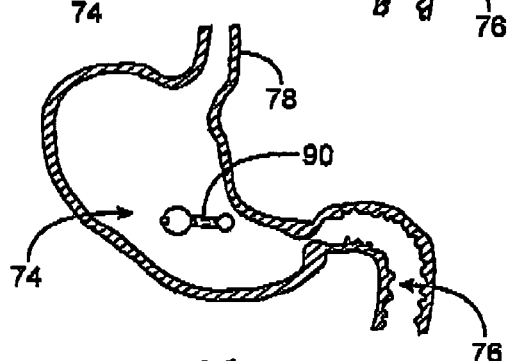
Figure 14C:
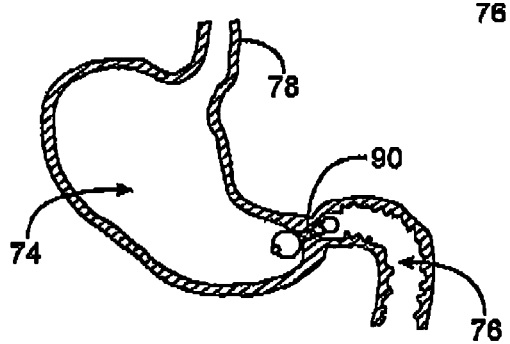
Figure 14D:
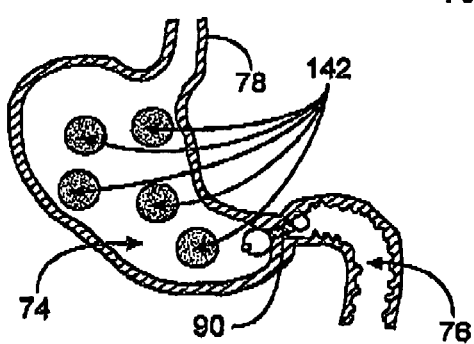

FIGS. 14A to 14D show cross-sectional views of yet another alternative use of devices of the present invention. As shown in FIGS. 14A to 14C, a device 90 may be placed to occlude the pyloric valve. In this case, the device 90 is shown as having been ingested, although placement of the device 90 may be affected via any of the methods described above. As shown in FIG. 14D, the addition of one or several gastric fillers 142, e.g., inflatable gastric balloons, expandable scaffolding, or any other number of space-occupying devices generally known in the art, may be utilized. In this variation, the device 90 may be placed and then the gastric fillers 142 may be introduced. The device 90 may be utilized to ensure that the gastric fillers 142 are not passed through the pyloric valve until they are sufficiently small, thereby allowing for non-degradable substances to be utilized without the concomitant risk of small bowel obstruction.

Figure 15A:
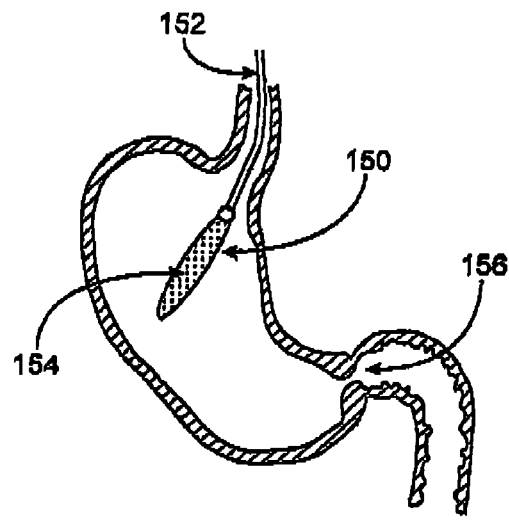
FIGS. 15A to 15D show cross-sectional views of a device designed to partially displace intragastric volume and intermittently obstruct a gastric opening, according to one embodiment of the present invention.
Figure 15B:
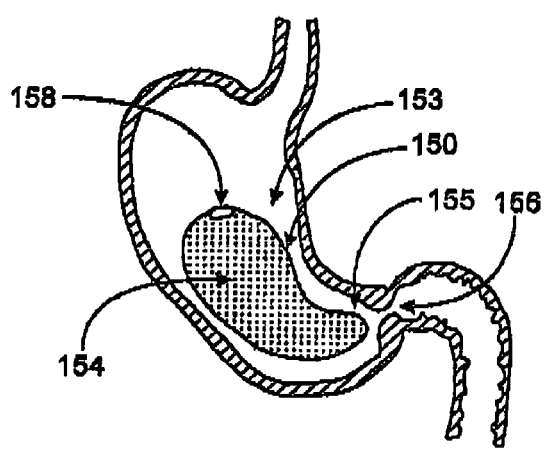

FIGS. 15A to 15D are cross-sectional views demonstrating the use of another embodiment of a device 150 for intermittently obstructing a pyloric valve 156, and in this embodiment for partially filling the gastric space. FIG. 15A illustrates the device 150 in an unexpanded or uninflated state and ready for delivery and/or insertion into the stomach via a catheter device 152, such as an endoscope, tubing or the like. The device, in this embodiment, includes an expandable foam 154, which is expanded when the device 150 is within the stomach, as shown in FIG. 15B. Any suitable nontoxic liquids or gases may be introduced through an inflation port 158, for expanding the device 150 and/or the foam 154.

Any suitable materials may be used to form the device 150. In one embodiment, for example, the device 150 may comprise an expandable balloon fabricated from silicone, silicone elastomers, latex, polyurethane, PTFE, FEP, and/or the like. Alternatively, self-expanding materials, such as foam or hydrogels which typically expand upon contact with fluids, may be utilized within the device 150. If such self-expanding materials are utilized, they may be disposed in the device 150, and a fluid such as saline may be infused to expand the materials.

As shown in FIG. 15B, the device 150 in one embodiment includes a proximal portion 153 and a distal portion 155. In some embodiments, the proximal portion 153 has a supportive or structural function, for assuring that the device 150 has a large enough cross sectional diameter to prevent passage of the device 150 through the pyloric valve. Typically, the distal portion 155 functions to contact the pyloric valve 156 and/or tissue adjacent the pyloric valve 156, to intermittently and/or partially block the valve 156. In some embodiments, the distal portion 155 is made of compliant material, so that when it contacts stomach tissue in, around or adjacent the pyloric valve 156, it does not harm the tissue. In some embodiments the proximal portion 153 and distal portion 155 are made of the same material, with the proximal portion 153 having a greater amount of material, greater wall thickness or the like, relative to the distal portion 155.

Generally, the device 150 may have any of a number of suitable shapes, such as an irregular oblong shape as shown, an elongated spherical shape, a cone, a diamond or the like. In some embodiments, the shape is selected such that the device 150 naturally migrates toward the pyloric valve 156, with the distal portion 155 aligned to contact the valve 156. In these and other embodiments, migration of the device 150 to the valve 156 may be further enhanced by selecting a specific gravity or buoyancy of the device to allow it to move through the stomach contents towards the valve 156.

Figure 15C:
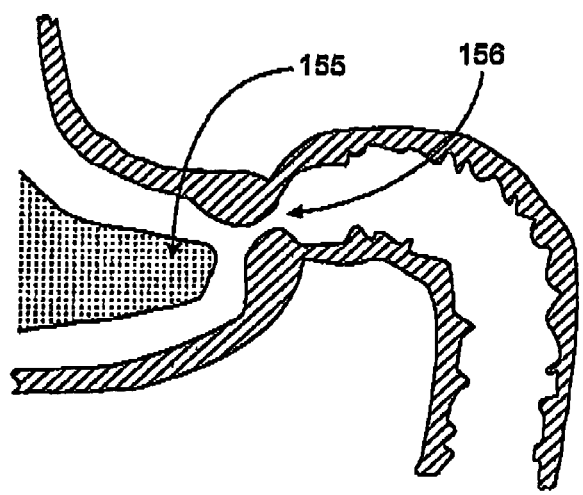
Figure 15D:
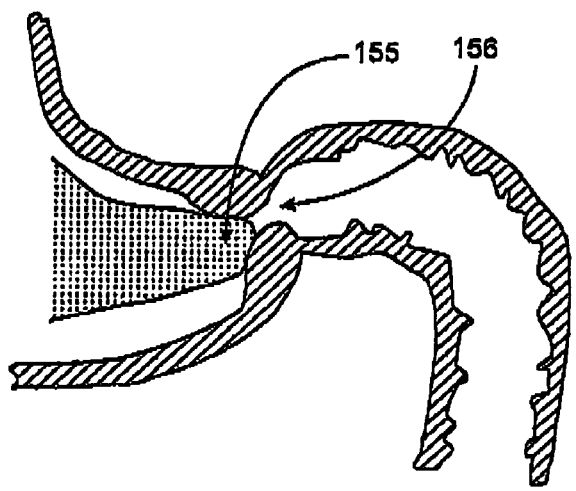

FIGS. 15C and 15D the distal portion 155 of the device 150 in interacting with the pyloric valve 156. As illustrated, the shape of the distal portion 155 is configured to move out of (FIG. 15C) and into (FIG. 15D) contact with the valve 156. This typically occurs during the natural contractions of the stomach, thus providing for intermittent obstruction of the pyloric valve 156. Intermittent obstruction of the pyloric valve 156 causes food in the stomach to be retained longer, and thus, feelings of satiation may be initiated sooner and may last longer, leading the patient to consume less food. In the embodiment shown in FIGS. 15C and 15D, the distal portion 155 fully obstructs the valve 156 when it is in contact. In alternative embodiments, the distal portion 155 may not fully obstruct the valve 156 and may have any of a number of various configurations designed to allow partial flow even when fully contacting the pyloric valve 156. For example, the distal portion 155 may have a shape such as conical, ellipsoid, spherical, pyramidal, tubular, disc-shaped with a protruding member (designed to fit within the pylorus) or the like. In one embodiment, the distal portion 155 and the proximal portion 153 have identical or nearly identical shapes, so that either end may obstruct the pyloric valve 156, regardless of the orientation of the device 150.

The device 150 may have any of a number of additional features for enhancing its delivery into the stomach, it ability to intermittently obstruct the pyloric valve 156, its removal from the stomach and/or the like. In one embodiment, for example, the device 150 includes one or more radiopaque markers, dyes and/or materials for facilitating visualization of the device 150. The device 150 may also include other markers, dyes or materials that enhance its visibility to the naked eye, which may be advantageous in embodiments where the device 150 dissolves and passes through the body or as a safety feature in the unlikely event that the device 150 breaks or ruptures.

In some embodiments, the device 150 may include one or more mechanisms for releasing one or more drugs into the stomach or small intestine beyond the pyloric valve. For example, slow-releasing drugs may be coupled with or infused into materials covering the device 150 or materials used to construct the device 150. These drugs, which may be any of a number of therapeutic or diagnostic agents, may slowly infuse into the patient by drug release into the intestinal tract or through contact with the patient. In other embodiments, the device 150 may incorporate electrical stimulation technologies. For instance, electrical probes may extend from a surface of the device 150 for insertion into the surrounding tissue or electrodes may be formed over a surface of the device 150.

In one embodiment, the device 150 may be covered by an erodable or biodegradable covering for delivery into the stomach. Such a covering may be configured to constrain the device 150, and once the covering comes into contact with substances in the gastric lumen, it may naturally break down and dissolve, thus releasing the device 150 and allowing it to expand. In one embodiment, the device 150 may be covered by different materials each configured to erode at differing rates or in different chemical environments within the stomach.

Figure 16:
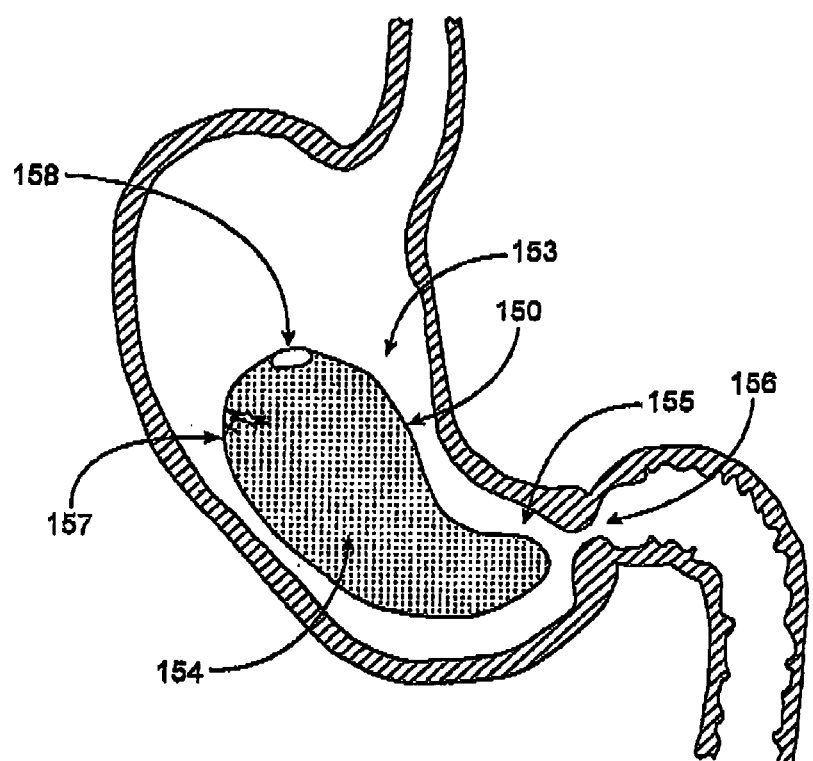
FIG. 16 shows a cross-sectional view of a device as in FIGS. 15A to 15D with a rupture.

FIG. 16 illustrates the device 150 of FIGS. 15A to 15D, in which a rupture 157 has occurred. As demonstrated by this figure, the overall shape of the device 150 is maintained due to expanded foam 154 (or other framework material or the like within or on the device 150 in other embodiments). Generally, the foam or framework material will be acid-resistant in order to prevent its degradation within the stomach and thus allow it to support the device 150 for extended periods of time after rupture has occurred. In an alternative embodiment, the foam 154 or other framework material may degrade slowly after rupture while releasing a signaling material that would alert the patient to the rupture upon examination of feces. The patient would then know to consult his physician to have the device 150 removed.

Figure 17A:
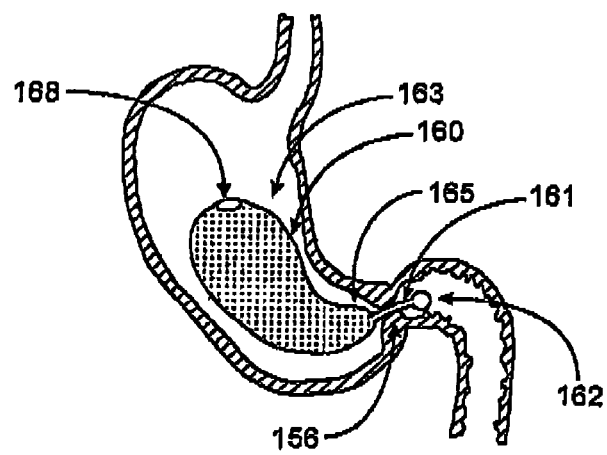
FIG. 17A shows a cross-sectional view of a device having a positioning member and a retaining member, according to one embodiment of the invention.
Figure 17B:
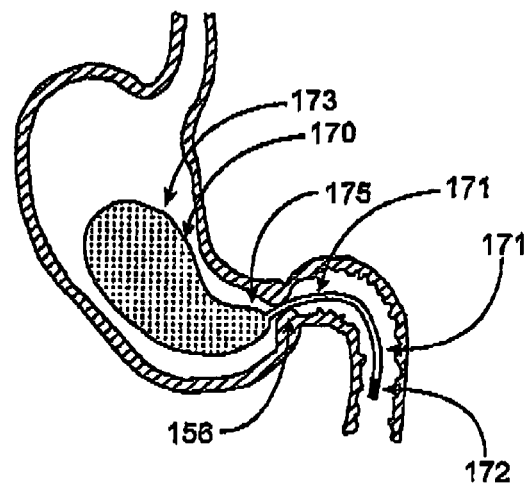
FIG. 17B shows a cross-sectional view of a device having a positioning member with an inflation port, according to one embodiment of the invention.

Referring now to FIGS. 17A and 17B, another embodiment of a pyloric valve obstructing device 160 may include and inflation port 168, a proximal portion 163, a distal portion 165, a positioning member 161 and a retaining member 162. Inflation port 168 is optional, of course, since some embodiments require inflation while others do not. Positioning member 161 generally helps position the device 160 in a location for intermittently obstructing the pyloric valve 156. Retaining member 162 helps maintain the location or position of the device 160.

In one embodiment, the positioning member 161 may be hollow, thus allowing for passage of fluids and/or gases through the device to allow the proximal portion 163, distal portion 165 and retaining member 162 to be inflated. In one embodiment, positioning member 161 may be relatively short, to inhibit movement of the distal portion 165 relative to the pylorus 156. In other embodiments, the positioning member 161 may be longer to allow for more movement of the device 160.

Referring now to FIG. 17B, in another embodiment a device 170 having proximal 173 and distal 175 portions is coupled with a positioning member 171 that includes an inflation port 172 at its distal end. In this embodiment, the device 170 is passed to the stomach in its uninflated state, the positioning member 171 and port 172 are used to inflate the device 170, and the positioning member is then swallowed and passes through the pyloric valve 156 to remain harmlessly in the first part of the small intestine. In another embodiment, the device may be placed into the stomach while attached to a removable tether that extends up the esophagus and into the mouth. The tether can be used to remove the device if it does not properly deploy, or alternatively it can be detached from the device once it is in place in the stomach.

Figure 18A:
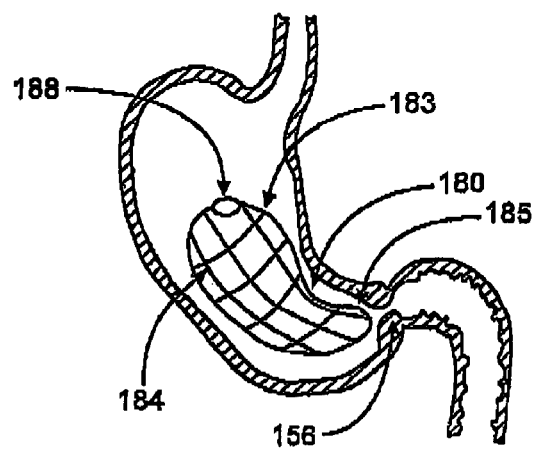
FIGS. 18A and 18B show cross-sectional views of two different embodiments of a device for obstructing a pyloric valve, according to two embodiments.
Figure 18B:
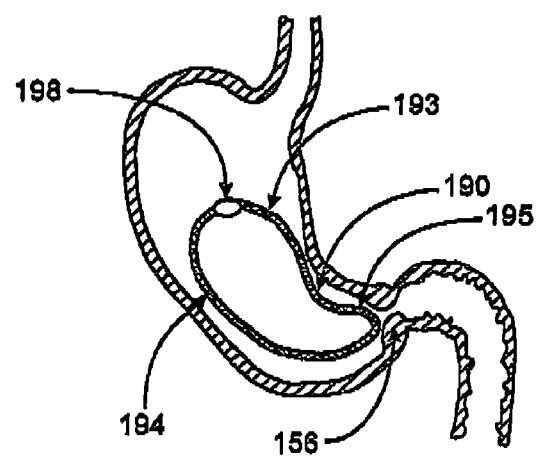

As illustrated in FIGS. 18A and 18B, and as mentioned earlier, various embodiments of a device for obstructing a pyloric valve may include any of a number of different expandable support mechanisms. The embodiments just described included foam, but other supportive structures and materials may be used, such as self-expanding cages, coils, lattices, frameworks or the like. In FIG. 18A, a device 180 having proximal 183 and distal 185 portions as well as an inflation port 188 also includes an expanding scaffolding 184, which may be coupled with the wall of the device 180 on its inner surface or outer surface, or which may be embedded in the wall. Such an expanding scaffolding 184 may be composed of shape memory or super-elastic materials, such as Nitinol. The scaffold 184 may be compressed into a delivery configuration and then either allowed to expand into the desired occlusive shape by self-expansion or expanded by supplying an activation energy, such as, electrical energy, heat, RF energy or the like. In another embodiment, the scaffold may be deployed by pulling the scaffold into an expanded configuration with a pulling device, and in such embodiments the scaffold may have a catch mechanism to prevent it from collapsing to its original shape.

In the embodiment shown in FIG. 18B, a device 190 includes a proximal portion 193, a distal portion 195 and an inflation port 198. In this embodiment, a wall 194 of the device 190 is made of a shape memory, super-elastic or otherwise self-expanding material, which expands from a smaller configuration to a larger configuration upon release from constraint. The material of the wall 194 then retains its expanded shape, thus maintaining the shape of the device 190 and preventing the device from collapsing.

Figure 19B:
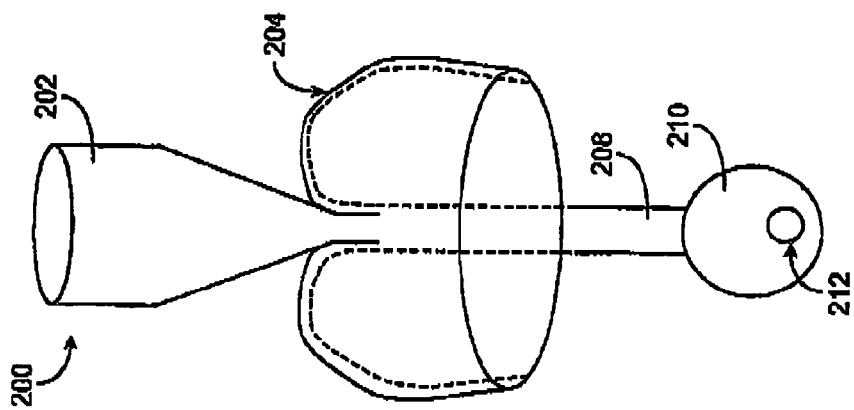
FIGS. 19A and 19B show side views of an device for obstructing a pyloric valve, according to another embodiment.
Figure 19A:
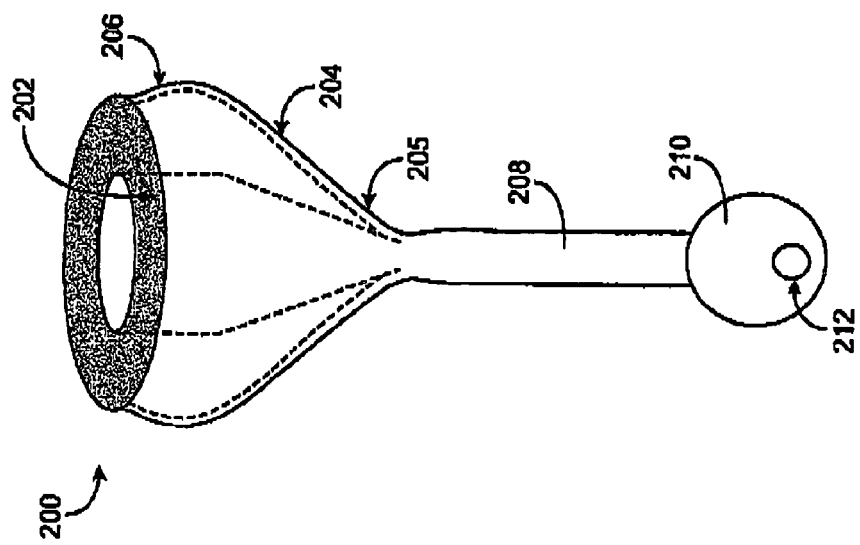

Referring to FIGS. 19A and 19B, another embodiment of a pyloric valve obstructing device 200 includes a movable or "inverted" outer shell 204, an inner core 202, a positioning member 208 and a distal retaining member 210 having a hole 212 or other surface feature. The device 200 is shown in its expanded configuration in FIG. 19A, for intermittently obstructing a pyloric valve, and in its collapsed configuration in FIG. 19B, for delivery into the stomach. The shell 204 includes a tissue contacting/engaging portion 205 and a support portion 206. Generally, the support portion 206 is more rigid/stiffer than the tissue contact portion 205, so that the former helps maintain the cross-sectional diameter of the device 200 so that it cannot pass through the pylorus, while the latter is more compliant so that it can contact stomach tissue without causing significant damage.

The various components of the device 200 may be constructed of any suitable materials, such as those already described or any other suitable materials now known or hereafter discovered. In one embodiment, the inner core 202 is a solid material, such as silicone, but in other embodiments the core 202 may be hollow. The core 202 may have any suitable size, shape, cross-sectional diameter or the like. In one embodiment, the core 202 has a cross-sectional diameter of between about 5 mm and about 30 mm, and preferably about 10 mm. The shell 204 may be made of the same or different material as the core 202, and also may have any suitable size, shape, cross-sectional diameter or the like. In one embodiment, the support portion 206 of the shell 204 is thicker that the tissue contact portion 205. In other embodiments, the support portion 206 may be made of a different material than the tissue contact portion 205.

The positioning member 208 may be an extension of inner core 202, shell 204 or both, or may instead be a separate piece coupled with the inner core 202 and/or outer shell 204. Positioning member 208 may have any suitable length and diameter to allow it to pass through the pyloric valve. In one embodiment its cross-sectional diameter is about 1.0 cm or less and its length is about 3.0 cm or greater. The retaining member 210 may also have any suitable size, shape or configuration, with some embodiments being expandable, some being self-expanding, and others configured to not expand at all. In one embodiment, the retaining member 210 has a greatest cross-sectional diameter of about 30 mm or smaller, and preferably about 25 mm or smaller, and even more preferable about 21 mm or smaller. The hole 212 or surface feature in the retaining member 210 may have any configuration for allowing coupling of an actuator or other device with the retaining member for delivering, adjusting and/or retrieving the device 200. Both the positioning member 208 and the retaining member 210 may be made of any suitable material.

Although not drawn to scale, FIG. 19B illustrates the collapsed or inverted state of the device 200. In this configuration, the shell 204 may be compressed to a smaller cross-sectional diameter for delivery, such as through a delivery tube or catheter. After the device 200 is delivered to the stomach, the shell 204 is inverted to its expanded state and the device 200 may then act to intermittently obstruct the pyloric valve.

FIGS. 20A to 20C illustrate a method for delivering and deploying the device 200 of FIGS. 19A and 19B in a stomach. In FIG. 20A, the device 200 is housed within the lumen of a delivery tube 214 or catheter in its collapsed configuration. In FIG. 20B, the device has been advanced partially out of the delivery tube, allowing the shell 204 to at least partially expand. An actuator 216 hooked through the hole 212 on the retaining member 210 may then be used to pull back on the device 200, such that the shell 204 overlaps the distal end of the delivery tube 214. The distal end of the delivery tube 204 is then used to apply force to the shell 204, causing it to invert into its expanded state, as shown in FIG. 20C. As also shown in FIG. 20C, the actuator 216 may include a hook 218 for coupling with the hole 212 in the retaining member 210. Once the shell 204 is moved to its expanded configuration, it is designed to stay in that configuration, thus providing the pyloric valve contacting and device retention functions described above. In one embodiment, the delivery tube 214 may include an expandable balloon (not shown) at or near its distal end. The balloon maybe doughnut-shaped to inflate circumferentially, or may be have an eccentric shape or any other suitable shape. The balloon may be inflated and serve as a stop against which the device 200 may be pulled. Alternatively, the balloon may be inflated under or within the device 200 to invert the device 200 as the balloon inflates.

In other embodiments, the device may be delivered and/or deployed using any other suitable method. For example, in one embodiment the shell 204 may "self-invert" from its constrained/collapsed state to its expanded state without using an actuator 216 or the distal end of a delivery device 214. Self-inverting may be achieved by shape-memory or spring loaded materials or the like, or by a shell geometry that creates a bias in the stiffness of the device. In another embodiment, the device 200 may be swallowed, either in a folded or otherwise collapsed state or housed within a dissolving caplet. A number of different alternative embodiments are possible.

Figure 21:
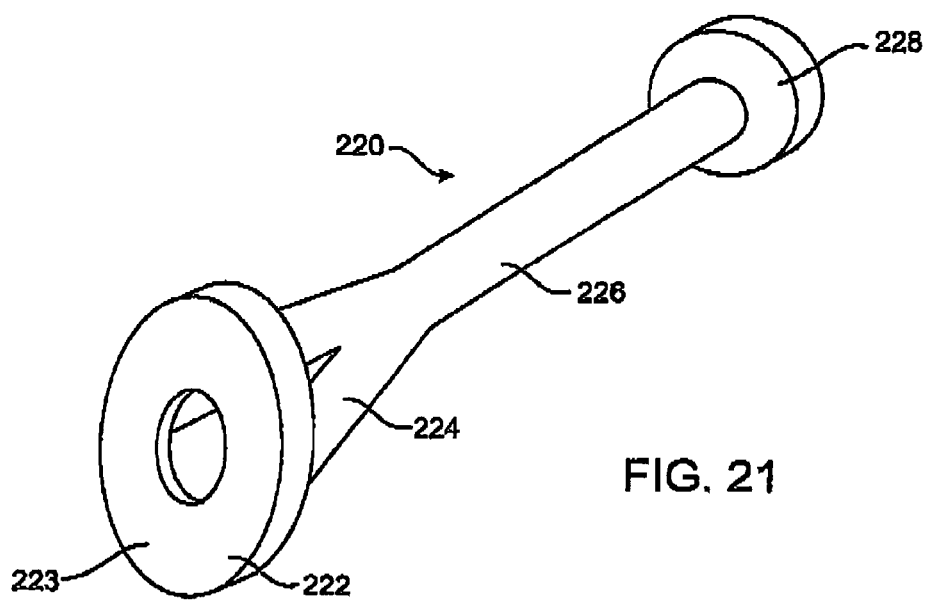
FIG. 21 illustrates a non-obstructing gastrointestinal anchoring device according to one embodiment of the present invention.

FIG. 21 shows an embodiment of a gastrointestinal anchoring device 220 that, unlike devices described above, is not adapted to obstruct the pyloric valve. Instead, device 220 includes a stomach retention member 222 with an opening 223 to allow passage of food, a tissue contacting portion 224 that does not block the pyloric valve, a valve spanning member 226 and a distal anchor member 228. Stomach retention member 22 is sized and will have sufficient rigidity and strength to prevent its passing through the pyloric valve and to prevent its collapse. Tissue contact member 224 and valve spanning member 226 are sized and configured such that they do not block passage of food through the pyloric valve. And distal anchor member 228 is sized to resist passing back through the pyloric valve into the stomach. In some embodiments, distal anchor member 228 is small enough to pass from the stomach through the pyloric valve naturally but still resists passing back through the valve. In other embodiments, the distal anchor member 228 must be placed (via applying pressure to push member 228 through the valve or via surgery) beyond the pyloric valve. Thus, anchoring device 220 maintains itself within a portion of the stomach, crossing over the pyloric valve into the duodenum, and does so without attaching directly to stomach tissue, but instead by intermittently contacting stomach tissue.

In one embodiment, stomach retaining portion 222, pyloric valve spanning member 226 and/or distal anchor member 228 may be adapted to change configurations while the device resides in the gastrointestinal tract. For example, in some embodiments, pyloric valve spanning member 226 changes its length and/or its diameter. Such configuration changes may be triggered by receipt and processing of one or more signals by a receiver and processor of the device. For example, signals may be transmitted by one or more external or internally implanted devices adapted to transmit radiofrequency, electromagnetic, microwave or ultrasound signals. Alternatively, configuration changes may be triggered upon sensing of pH, temperature, bile content, nutrient content, fats, sugars, alcohol, opiates, drugs, analytes, electrolytes and/or hemoglobin by at least one sensor of the device.

Figure 22:
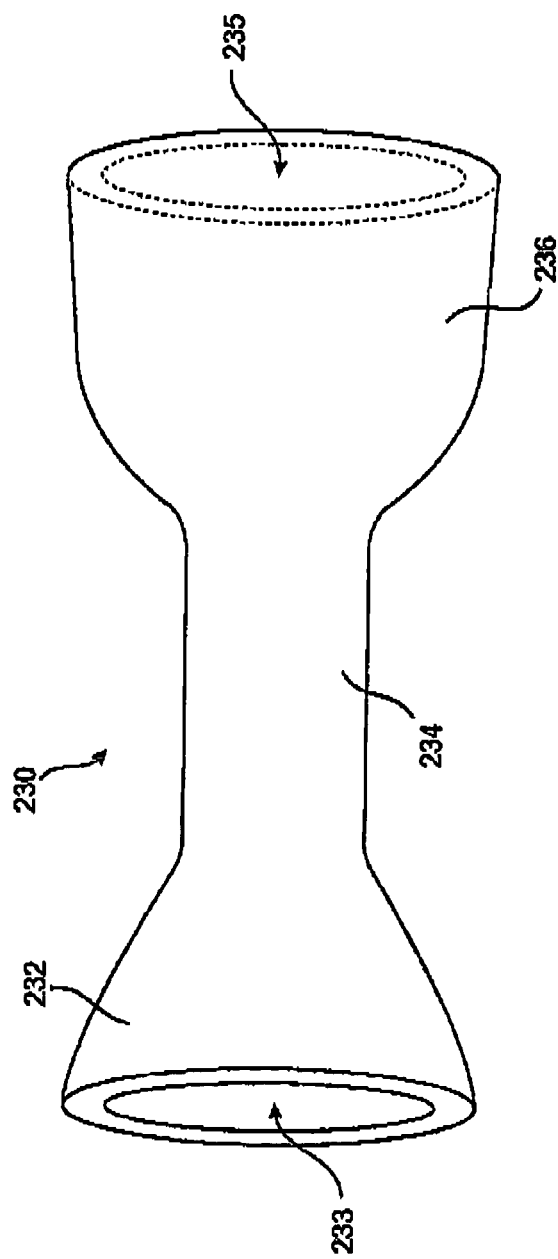
FIG. 22 illustrates a non-obstructing gastrointestinal anchoring device according to another embodiment of the present invention.

FIG. 22 shows another embodiment of an anchoring device 230, in this case including a combined stomach retention/tissue contacting portion 232, a pyloric valve spanning portion 234 and a distal anchor portion 236. The device 230 is hollow, with a proximal opening 233 in the stomach retention portion 232 in fluid communication with a distal opening 235 in the distal anchor portion 235. Valve spanning portion 234 is sized such that it does not force open the pyloric valve, and in some embodiments it is collapsible, thus distinguishing device 230 from other sleeve-like, pyloric valve spanning devices. In some embodiments, distal anchor portion may be formed of stent material, such as Nitinol. Again, however, device 230 does not directly attach itself to gastrointestinal wall tissue but instead is free to move backwards and forwards through the pyloric valve, thus intermittently contacting stomach wall tissue without direct attachment thereto. In some embodiments, device 230 may also include a sleeve (not shown) extending from distal anchor portion 236 and in fluid communication with distal opening 235. Such a sleeve may extend along a portion of the small intestine to prevent or reduce absorption of nutrients along the length, thus helping to treat obesity.

Figure 23:
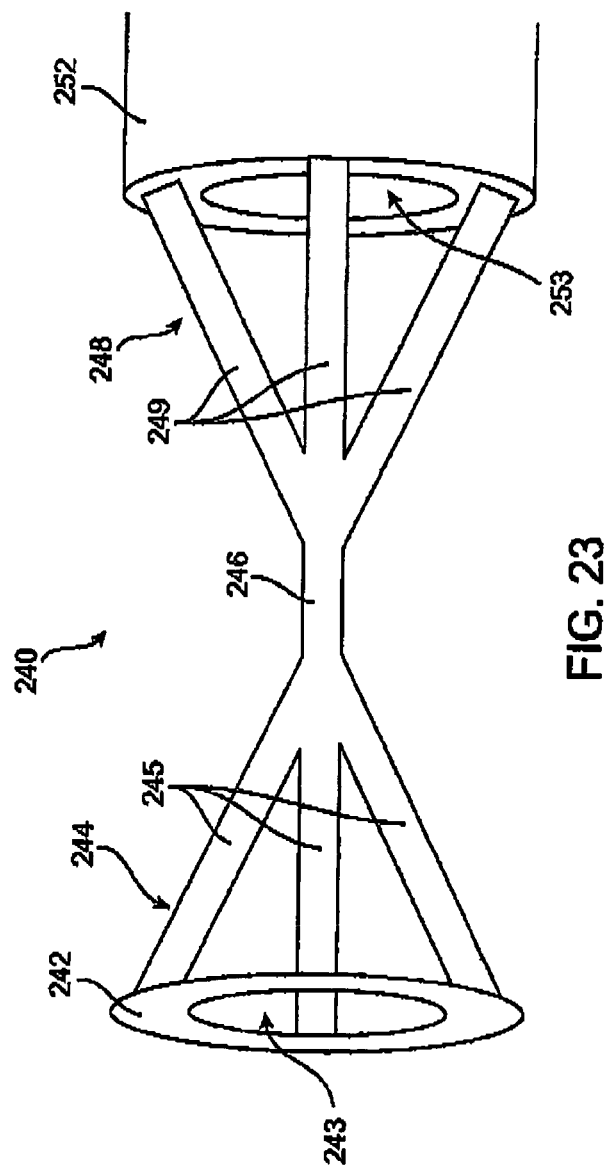
FIG. 23 illustrates a non-obstructing gastrointestinal anchoring device coupled with an intestinal sleeve according to another embodiment of the present invention.

FIG. 23 shows another embodiment of an anchoring device 240 having a stomach retention member 242 with an opening 243, a tissue contacting portion 244 with multiple arms 245, a pyloric valve spanning portion 246, a distal anchor portion 248 including multiple tethers 249, and a distal sleeve 252 coupled to device 240 via tethers 249. Again, in this embodiment device 240 does not obstruct the pyloric valve, or at most obstructs it only minimally. Food passes through the valve, and at least some of the food then passes into sleeve 252 via a proximal sleeve opening 253. Food then passes through sleeve, which prevents or at least reduces absorption of nutrients by the intestine along the length of sleeve 252.

Any of the embodiments described above with reference to FIGS. 1-23 may include one or more actuators, one or more sensors, or a combination of both. Such actuators and sensors may be coupled with any portion of an anchoring device, pyloric corking device or the like, such as any portions residing in the stomach, spanning the pyloric valve or disposed within the duodenum. In some embodiments, one or more actuators or sensors are coupled with an anchoring device or corking device via one or more tethers, while in other embodiments all the actuators and/or sensors may be attached directly to the anchoring device.

One type of actuator that may be coupled with an anchoring device is an energy transmission member for applying energy to gastrointestinal tissue, such as but not limited to radiofrequency, ultrasound, microwave, cryogenic, laser, light, electrical, mechanical or thermal energy. Another type of actuator is a substance (or substances) releasably coupled with the anchoring device, such as but not limited to lipids, drugs, enzymes, diagnostic agents, lipids, vitamins, minerals or the like. Such substances may be releasably coupled with an outer surface of the anchoring device or may be housed within one or more refillable reservoirs. A space-occupying member for occupying space in the stomach to enhance the patient's feeling of satiety is another type of actuator. Yet another example of an actuator is a trigger adapted to elicit a biological response, such as a surface coating adapted to induce a satiety response. Any suitable imaging device may be another type of actuator. Generally, any suitable device for performing a function from within the gastrointestinal system may be coupled with the anchoring devices and pyloric corking devices of the present invention according to various embodiments.

In some embodiments, an anchoring device may further include at least one sensor coupled with the anchoring member for sensing one or more characteristics in the gastrointestinal tract. Such a sensor (or sensors) may be adapted to sense, for example, pH, temperature, bile content, nutrient content, fats, sugars, alcohol, opiates, drugs, analytes, electrolytes and/or hemoglobin. Such an embodiment may further include a processor adapted to process data related to the sensed signals and provide the processed data to the at least one actuator. These or other embodiments may also include a receiver for receiving transmitted data from a remote source, a transmitter for transmitting data, a data storage module, a rechargeable power source, or any suitable combination thereof.

As was described above, in some embodiments an anchoring and/or pyloric corking device may be delivered via an elongate catheter device, such as an orogastric or nasogastric tube, passed through the patient's esophagus into the stomach. That same delivery catheter device or a separate device may also be adapted for use in modifying, adjusting and/or recharging an anchoring or corking device once it is in place in the stomach. This would allow a device to be modified without removing the device or requiring device replacement.

Figure 24:
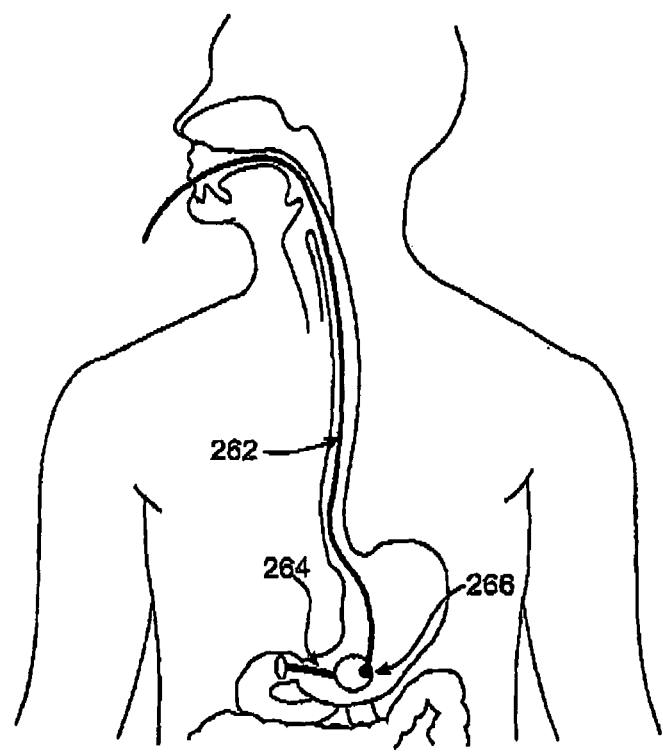
FIG. 24 illustrates an elongate catheter device coupled with an anchoring device according to one embodiment of the present invention.
Figure 25:
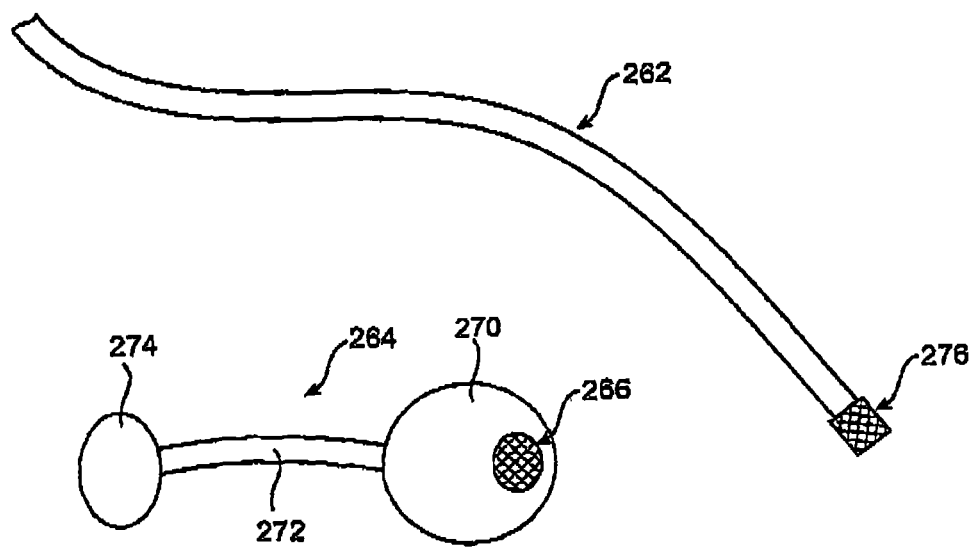
FIG. 25 illustrates in greater detail the elongate catheter device and anchoring device shown in FIG. 24.

FIGS. 24 and 25 show an embodiment of an elongate catheter device 262 and attachable anchoring device 264 such as just described. Anchoring device 266 includes an attachment member 266 by which catheter device 262 may attach to anchoring device 264. In some embodiments, for example, as seen more clearly in FIG. 25, catheter device 262 includes a magnetic distal tip member 276, and attachment member 266 on anchoring device 264 is an oppositely charged magnet coupled with a stomach retention portion 270 of device 264. (Anchoring device 264 also includes a pyloric valve spanning portion 272 and a distal anchor portion 274.) Elongate catheter device 262 may be used to perform any suitable function, according to various embodiments, such as but not limited to recharging a power source, refilling one or more drug reservoirs, changing a location or orientation of anchoring device 264, changing a configuration of one or more portions of anchoring device 264, inflating or deflating one or more portions of anchoring device 264 and/or the like. In some embodiments, catheter device 262 may work in conjunction with a remote transmitter located outside the patient or implanted within the patient to provide additional instructions, adjustments, power or the like to anchoring device 264.

Although the above is a complete and accurate description of the invention, any of a number of variations, additions and the like may be made to the embodiments described without departing from the scope of the invention. For example, devices and methods described above may be used to treat any suitable condition or perform any suitable function within the gastrointestinal tract. Therefore, the foregoing description is provided primarily for exemplary purposes and should not be interpreted to limit the scope of the invention as it is defined in the following claims.

What is claimed is:

1. A device for performing one or more functions in a gastrointestinal tract of a patient, the device comprising:
   a first anchoring member adapted to maintain a deployed configuration having a fixed shape within a pyloric portion of the patient's stomach and to intermittently engage, without directly attaching to, stomach tissue such that the first anchoring member is proximally translatable relative to a pyloric valve whereby a passage between the first anchoring member and the pyloric valve is opened intermittently;
   a tissue contacting portion extending from the first anchoring member comprising two or more members which have an opened configuration;
   a spanning member having a proximal end attached to the two or more members of the tissue contacting portion and further having a shape adapted to pass at least partially through the pyloric valve;
   a second anchoring member coupled to a distal end of the spanning member for maintaining the first anchoring member in intermittent contact with the pyloric valve and further having a shape sized for passage through the pyloric valve after deployment; and
   at least one actuator coupled with the first anchoring member and actuated from within the stomach for performing a function from within the patient's gastrointestinal tract.

2. A device as in claim 1, wherein the first anchoring member comprises a stomach retention portion having sufficient size and rigidity to prevent passage of the stomach retention portion through the pyloric valve.

3. A device as in claim 2, wherein at least one actuator is coupled with the stomach retention portion.

4. A device as in claim 2, wherein the stomach retention portion is expandable from a first configuration for delivery through an esophagus of the patient to a second configuration for preventing passage of the stomach retention portion through the pyloric valve.

5. A device as in claim 2, wherein the first anchoring member further includes a tissue engagement portion adapted to intermittently engage pyloric stomach tissue without causing significant damage to the tissue.

6. A device as in claim 5, wherein at least one actuator is coupled with the tissue engagement portion.

7. A device as in claim 5, wherein the tissue engagement portion comprises at least one compliant material.

8. A device as in claim 1, wherein the at least one actuator is coupled with the spanning member.

9. A device as in claim 1, wherein the second anchoring member is adapted to reside in a duodenum of the patient.

10. A device as in claim 1, wherein the at least one actuator is coupled with spanning member and the second anchoring member.

11. A device as in claim 1, wherein at least one actuator is coupled with the second anchoring member and is adapted to extend into a small intestine of the patient.

12. A device as in claim 1, wherein at least one of the first anchoring member, the spanning member and the second anchoring member is adapted to change configurations while residing in the gastrointestinal tract.

13. A device as in claim 12, wherein the spanning member is adapted to change its length.

14. A device as in claim 12, wherein the spanning member is adapted to change its diameter.

15. A device as in claim 1, further comprising an attachment mechanism for attaching to a catheter device extended into the stomach to adjust or modify the device.

16. A device as in claim 15, wherein the attachment mechanism comprises a magnet.

17. A device as in claim 1, wherein the first anchoring member includes at least one passage for allowing substances to pass through the device.

18. A device as in claim 1, wherein the at least one actuator comprises one or more substances releasably coupled with the device.

19. A device as in claim 18, wherein the one or more substances are selected from the group consisting of lipids, drugs, enzymes, diagnostic agents, lipids, vitamins, and minerals.

20. A device as in claim 18, wherein the at least one substance is releasably coupled with at least one outer surface of the device such that the substance automatically releases from a surface over time.

21. A device as in claim 20, further comprising a substrate coupled with an outer surface for releasably coupling the at least one substance with the device.

22. A device as in claim 18, wherein the at least one substance is housed within at least one reservoir on the device.

23. A device as in claim 22, wherein the at least one substance is automatically released from the at least one reservoir over time.

24. A device as in claim 22, wherein the at least one substance is released from the at least one reservoir when the device receives a signal from a transmitter outside the patient.

25. A device as in claim 22, wherein the at least one reservoir is adapted to be refilled while the device resides in the gastrointestinal tract.

26. A device as in claim 25, wherein the reservoir are adapted to be refilled via a catheter device passed into the stomach via an esophagus of the patient.

* * * * *